United States Patent
Platzek et al.

(10) Patent No.: US 6,461,587 B1
(45) Date of Patent: Oct. 8, 2002

(54) PERFLUOROALKYLAMIDES, THEIR PRODUCTION AND THEIR USE IN DIAGNOSIS

(75) Inventors: Johannes Platzek; Ulrich Niedballa; Detlev Suelzle, all of Berlin; Wolfgang Schlecker, Altdorf; Bernd Raduechel, Berlin; Hanns-Joachim Weinmann, Berlin; Thomas Frenzel, Berlin; Bernd Misselwitz, Glienicke; Wolfgang Ebert, Mahlow, all of (DE)

(73) Assignee: Schering Aktiengesellschaft (DE)

( * ) Notice: Subject to any disclaimer, the term of this patent is extended or adjusted under 35 U.S.C. 154(b) by 0 days.

(21) Appl. No.: 09/533,178

(22) Filed: Mar. 22, 2000

Related U.S. Application Data

(60) Provisional application No. 60/128,623, filed on Apr. 9, 1999.

(30) Foreign Application Priority Data

Mar. 22, 1999 (DE) ............................................. 199 14 101

(51) Int. Cl.$^7$ ............................................... A61B 5/055
(52) U.S. Cl. ......................... 424/9.323; 534/7; 534/14; 424/9.1; 424/9.3; 424/9.32; 424/9.4; 424/9.42
(58) Field of Search ................................ 424/1.11, 1.65, 424/9.1, 9.3, 9.32, 9.323, 9.4, 9.42, 9.5, 9.6; 534/7, 10–16; 540/470, 474

(56) References Cited

U.S. PATENT DOCUMENTS 5,690,909 A 11/1997 Platzek et al.

FOREIGN PATENT DOCUMENTS

| DE | 43 17 588 | 12/1994 |
|---|---|---|
| DE | 196 03 033 | 7/1997 |
| DE | 196 08 278 | 8/1997 |

OTHER PUBLICATIONS

Derwent world patents abstract of 196 08 278.
Derwent world patents abstract of 196 03 033.

*Primary Examiner*—Dameron L. Jones
(74) *Attorney, Agent, or Firm*—Milen, White, Zelano & Branigan, P.C.

(57) ABSTRACT

The invention relates to macrocyclic perfluoroalkylamides, their production and their use in diagnosis.

19 Claims, 2 Drawing Sheets

PERFLUOROALKYLAMIDES, THEIR PRODUCTION AND THEIR USE IN DIAGNOSIS

This application claims the benefit of the filing date of U.S. Provisional Application Serial No. 60/128,623 filed Apr. 9, 1999.

The invention relates to the subject that is characterized in the claims, i.e., macrocyclic perfluoroalkylamides, their production and their use in diagnosis.

In nuclear magnetic resonance, the element fluorine is second in importance to the element hydrogen.

1. Fluorine has a high sensitivity of 83% of that of hydrogen.
2. Fluorine has only one NMR-active isotope.
3. Fluorine has a resonance frequency that is similar to hydrogen—fluorine and hydrogen can be measured with the same system.
4. Fluorine is biologically inert.
5. Fluorine does not occur in biological material (exception: teeth) and can therefore be used as a probe or contrast medium against a background that is free of interfering signals.

The effect of these properties is that fluorine occupies a broad space in diagnostic patent literature with nuclear magnetic resonance as a basis: fluorine-19-imaging, functional diagnosis, spectroscopy.

U.S. Pat. No. 4,639,364 (Mallinckrodt) thus proposes trifluoromethanesulfonamides as contrast media for fluorine-19-imaging:

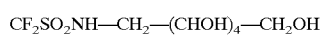

German Patent DE 4203254 (Max-Planck-Gesellschaft), in which an aniline derivative is proposed, also relates to fluorine-19-imaging:

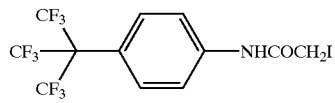

Fluorine-19-imaging is the subject of application WO 93/07907 (Mallinckrodt), in which phenyl derivatives are also claimed as contrast media:

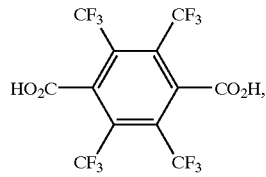

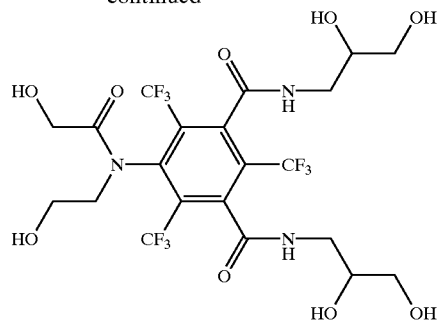

Compounds of considerably simpler structure are also claimed for fluorine-19-imaging. Thus, U.S. Pat. No. 4,586,511 (Children's Hospital Medical Center) mentions perfluorooctyl bromide

European Patent EP 307863 (Air Products) mentions perfluoro-15-crown-ether

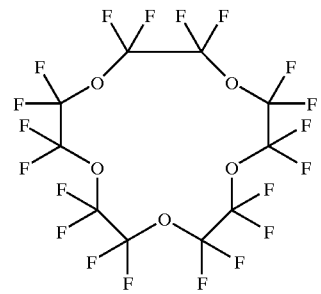

and U.S. Pat. No. 4,588,279 (University of Cincinnati, Children's Hospital Research Foundation) mentions perfluorocarbon compounds, such as perfluorocyclononane or -octane, perfluorinated ethers such as tetrahydrofuran

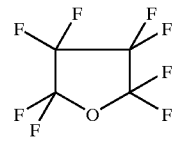

or diethers such as perfluoro-propyleneglycol-diether

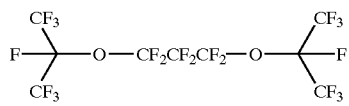

The compounds that are mentioned in Application WO 94/22368 (Molecular Biosystems), e.g.,

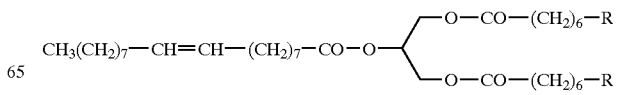

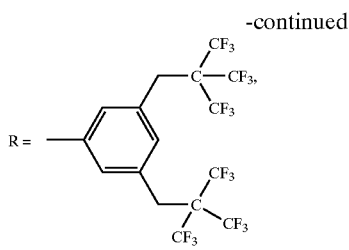

which as fluorine-containing radicals have the perfluoro-1H, 1H-neopentyl group, are also used for fluorine-19-imaging.

U.S. Pat. No. 5,362,478 (VIVORX) indicates another structural type with expanded diagnostic use, in which the fluorocarbon/polymer shell combination is claimed for imaging purposes. Perfluorononane and human serum albumin are mentioned. This combination proves suitable, moreover, for using the fluorine atom as a probe for local temperature measurement and for determining the partial oxygen pressure.

Perfluorocarbons are also claimed in U.S. Pat. No. 4,586,511 for oxygen determination.

In German Patent DE 4008179 (Schering), fluorine-containing benzenesulfonamides are claimed as pH probes:

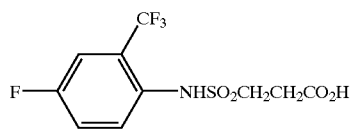

For NMR diagnosis, compounds that contain iodine and fluorine atoms are also claimed as contrast-enhancing agents in WO 94/05335 and WO 94/22368 (both molecular biosystems):

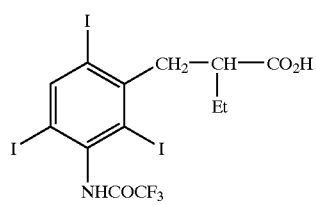

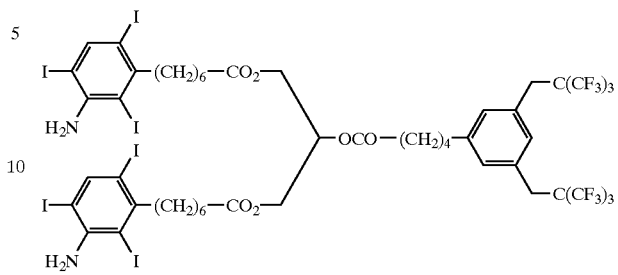

The fluorine-paramagnetic metal ion combination is also claimed for fluorine-19-imaging, specifically for open-chain complexes in WO 94/22368 (Molecular Biosystems) with, e.g.:

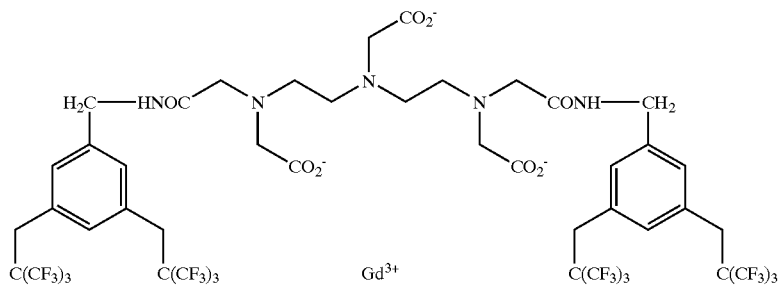

and in EP 292 306 (TERUM Kabushiki Kaisha) with e.g.:

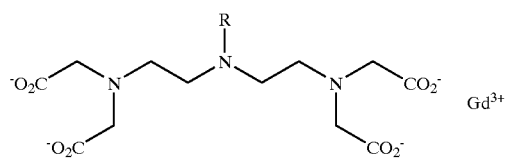

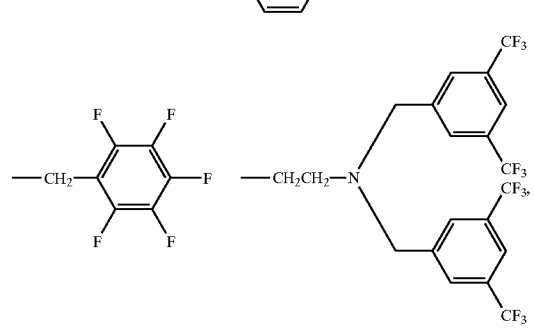

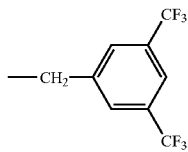

but also for cyclic compounds, as they are mentioned in EP 628 316 (TERUMO Kabushiki Kaisha)

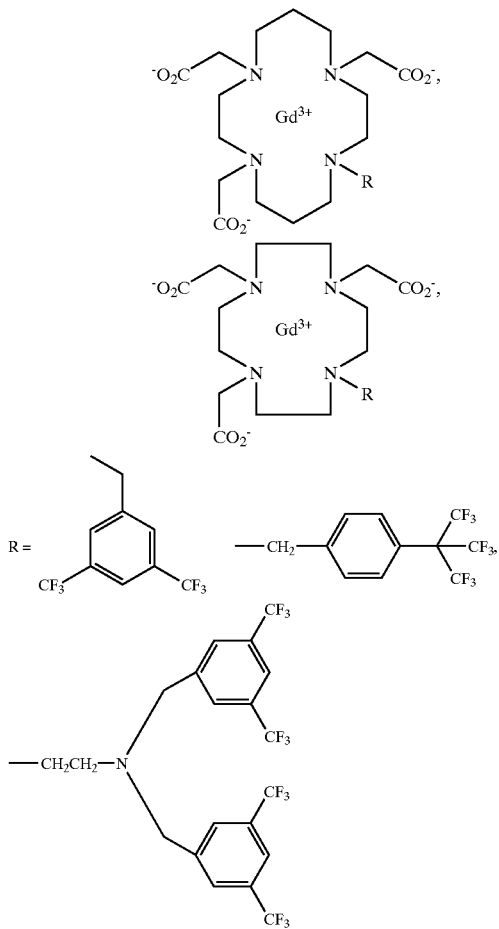

The fluorine atom-rare earth metal combination is also claimed for NMR-spectroscopic temperature measurements in DE 4317588 (Schering).

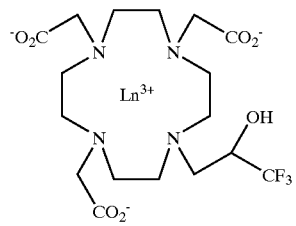

Ln: Rare earths: La, Pr, Dy, Eu

While no interactions between the two nuclei occur in compounds that contain the elements fluorine and iodine, intensive interaction does occur in compounds that contain fluorine and paramagnetic centers (radicals, metal ions), which are expressed in a shortening of the relaxation time of the fluorine nucleus. The extent of this effect depends on the number of unpaired electrons of the metal ion ($Gd^{3+}$>$Mn^{2+}$>$Fe^{3+}$>$Cu^{2+}$) and on the removal between the paramagnetic ion and the $^{19}F$ atom.

The more unpaired electrons of the metal ion are present and the closer they are brought to the fluorine, the greater the shortening of the relaxation time of the fluorine nucleus.

The shortening of the relaxation time as a function of the distance from the paramagnetic ion becomes apparent in all nuclei with an uneven spin number, thus also in the case of protons, and gadolinium compounds; therefore, there is wide use as contrast media in nuclear spin tomography (Magnevist[R], Prohance[R], Omniscan[R], Dotarem[R]).

In $^1H$-MR imaging ($^1H$-MRI), however, relaxation time $T^1$ or $T^2$ of the protons, i.e., mainly the protons of water and not the relaxation time of the fluorine nuclei, is measured and used for imaging. The quantitative measurement for the shortening of the relaxation time is relaxivity [L/mmol s]. Complexes of paramagnetic ions are successfully used for shortening the relaxation times. In the following table, the relaxivity of some commercial preparations is indicated:

| | $T^1$-Relaxivity in Water [L/mmol · s, 39° C., 0.47 T] | $T^1$-Relaxivity in Plasma [L/mmol · s, 39° C., 0.47 T] |
|---|---|---|
| MAGNEVIST[R] | 3.8 | 4.8 |
| DOTAREM[R] | 3.5 | 4.3 |
| OMNISCAN[R] | 3.8 | 4.4 |
| PRO HANCE[R] | 3.7 | 4.9 |

In these compounds, only interactions between protons and the gadolinium ion occur. For these contrast media in water, a relaxivity of about 4 [L/mmol·s] is thus observed.

Both fluorine compounds for fluorine-19-imaging, in which the shortened relaxation time of the fluorine nucleus is used, and non-fluorine-containing compounds, in which the relaxation time of the protons of water is measured, are thus used successfully for MR imaging.

In the introduction of a perfluorocarbon-containing radical into a paramagnetic contrast medium, i.e., in the combination of properties that were previously known as suitable only for fluorine-imaging compounds, the relaxivity that relates to the protons of water also increases rapidly, surprisingly enough, with compounds that were used for proton imaging. It now reaches values of 10–50 [L/mmol·s] in comparison to values between 3.5 and 3.8 [L/mmol·s] as they were already cited for some commercial products in the table above.

Perfluoroalkyl-containing metal complexes are known from DE 196 03 033.1. The compounds of this invention are distinguished, however, by better properties, such as, for example, higher lymph node accumulation in three successive lymph node stations, better elimination, greater compatibility (which is especially advantageous for i.v. lymphography) and very good local compatibility in the case of interstitial administration. This opens up the possibility of adding the compounds at higher doses.

The MRI contrast media are used mainly for the visualization of malignant tumors.

Malignant tumors metastasize in clusters in regional lymph nodes, whereby multiple lymph node stations may also be involved. Thus, lymph node metastases are found in about 50–69% of all patients with malignant tumors (Elke, Lymphographie [Lymphography], in: Frommhold, Stender, Thurn (Eds.), Radiologische Diagnostik in Klinik und Praxis [Radiological Diagnosis in Clinical Studies and Practice], Volume IV, Thieme Verlag Stuttgart, 7th Edition, 434–496, 1984)). The diagnosis of a metastatic attack of lymph nodes is of great importance with respect to the therapy and prognosis of malignant diseases. With modern imaging methods (CT, US and MRI), lymphogenous metastases of malignant tumors are detected only inadequately, since in most cases, only the size of the lymph node can be used as a diagnostic criterion. Thus, small metastases in non-enlarged lymph nodes (<2 cm) cannot be distinguished from lymph node hyperplasias without a malignant attack (Steinkamp et al., Sonographie und Kernspintomographie; Differential Diagnostik von reaktiver Lymphknotenvergr öβerung und Lymphknotenmetastasen am Hals [Sonography and Nuclear Spin Tomography: Differential Diagnosis of Reactive Lymph Node Enlargement and Lymph Node Metastases on the Neck], Radiol. Diagn. 33: 158, 1992).

It would be desirable if lymph nodes with metastatic attack and hyperplastic lymph nodes can be distinguished with use of specific contrast media.

Direct x-ray lymphography (injection of an oily contrast medium suspension into a prepared lymph vessel) is known as an invasive method that is used only infrequently and that can visualize only small lymphatic drainage stations.

Fluorescence-labeled dextrans are also used experimentally in animal experiments to be able to observe lymphatic drainage after their interstitial administration. All commonly used markers for the visualization of lymph tracts and lymph nodes after interstitial/intracutaneous administration have in common the fact that they are substances with a particulate nature ("particulates," e.g., emulsions and nanocrystal suspensions) or large polymers (see above, WO 90/14846). Based on their inadequate local and systemic compatibility as well as their small lymphatic passageway, which causes inadequate diagnostic efficiency, however, the previously described preparations prove to be still not optimally suitable for indirect lymphography.

Since the visualization of lymph nodes is of central importance for early detection of the metastatic attack in cancer patients, there is a great need for lymph-specific contrast medium preparations for diagnosis of corresponding changes of the lymphatic system.

The highest possible contrast medium concentration and high stability are just as desirable as the diagnostically relevant, most uniform possible lymphatic concentration over several lymph stations. The burden on the overall organism should be kept low by quick and complete excretion of the contrast medium. A quick start-up, if possible as early as within a few hours after the administration of contrast media, is important for the radiological practice. Good compatibility is necessary.

The object of the invention is achieved by the macrocyclic perfluoroalkyl compounds of general formula I

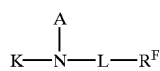

(I)

in which

K means a complexing agent or a metal complex of general formula II

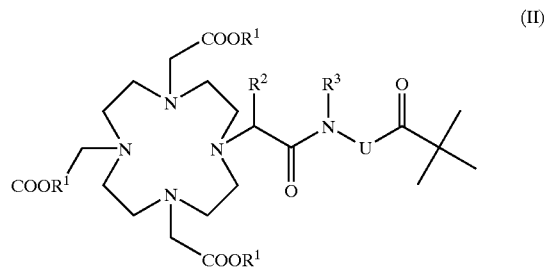

(II)

whereby
R$^1$ stands for a hydrogen atom or a metal ion equivalent of atomic numbers 21–29, 31, 32, 37–39, 42–44, 49 or 57–83,
R$^2$ and R$^3$ stand for a hydrogen atom, a $C_1$–$C_7$ alkyl group, a benzyl group, a phenyl group, —$CH_2OH$ or —$CH_2$—$OCH_3$, and
U stands for radical L, whereby L and U, independently of one another, can be the same or different,
A means a hydrogen atom, a straight-chain or branched $C_1$–$C_{30}$ alkyl group, which optionally is interrupted by 1–15 oxygen atoms and/or optionally is substituted with 1–10 hydroxy groups, 1–2 COOH groups, a phenyl group, a benzyl group and/or 1–5 OR$^4$ groups, with R$^4$ in the meaning of a hydrogen atom or a $C_1$–$C_7$ alkyl radical, or —L—R$^F$,
L means a straight-chain or branched $C_1$–$C_{30}$ alkylene group, which optionally is interrupted by 1–10 oxygen atoms, 1–5 —NH—CO groups, 1–5 —CO—NH groups, by a phenylene group that is optionally substituted by a COOH group, 1–3 sulfur atoms, 1–2 —N(B$^1$)—$SO_2$ groups, and/or 1–2 —$SO_2$—N(B$^1$) groups with B$^1$ in the meaning of A, an N(B)—$SO_2$ group or an —$SO_2$—N(B)— group, and/or optionally is substituted with radical R$^F$, and
R$^F$ means a straight-chain or branched perfluorinated alkyl radical of formula $C_nF_{2n}X$,
whereby 4 is equal to or less than n, which is equal to or less than 20, and
X stands for a terminal fluorine atom, chlorine atom, iodine atom or a hydrogen atom, and optionally present acid groups optionally can be present as salts of organic and/or inorganic bases or amino acids or amino acid amides.

The new perfluoroalkyl-containing compounds of general formula I of claim 1 according to the invention comprise both complexing agents and metal complexes. Compounds of general formula I in which the metal ion equivalent that is bonded in macrocycle K is absent are referred to as complexing agents, and compounds with a metal ion equivalent that is bonded in macrocycle K are referred to as metal complexes.

As metal ion equivalents, and depending on the desired use of the compounds according to the invention, the following metals are suitable:

1. When used in NMR diagnosis and x-ray diagnosis: complexes with the ions of elements with atomic numbers 21–29, 39, 42, 44 and 57–83;
2. When used in radiodiagnosis and radiotherapy: complexes with the radioisotopes of elements with atomic numbers 27, 29, 31, 32, 37–39, 43, 49, 62, 64, 70, 75 and 77.

The ions of elements with atomic numbers 21–29, 39, 42, 44 and 57–83 are preferred.

Gadolinium is especially preferred.

Alkyl groups $R^2$, $R^3$, $R^4$ can be straight-chain or branched. Methyl, ethyl, propyl, isopropyl, n-butyl, 1-methylpropyl, 2-methylpropyl, n-pentyl, 1-methylbutyl, 2-methylbutyl, 3-methylbutyl, 1,2-dimethylpropyl can be mentioned by way of example.

Hydrogen and $C_1$–$C_4$ alkyl groups, especially preferably hydrogen and the methyl group, are preferred for $R^2$, $R^3$ and $R^4$.

The benzyl group and phenyl group $R^2$, A and $B^1$ can be substituted in the phenyl ring. As a substrate, the COOH group is suitable.

If the compound of formula I contains radicals L and U at the same time, L and U can be different from one another.

The $C_1$–$C_{30}$ alkylene groups U can be straight-chain or branched. Methylene, ethylene, propylene, isopropylene, n-butylene, 1-methylpropylene, 2-methylpropylene, n-pentylene, 1-methylbutylene, 2-methylbutylene, 3-methyl-butylene, 1,2-dimethylpropylene can be mentioned by way of example.

For U in the meaning of alkylene, $C_1$–$C_{10}$ alkylene groups are preferred; $C_1$–$C_4$ alkylene groups are especially preferred.

The $C_1$–$C_{30}$ alkyl groups A can be straight-chain or branched. Methyl, ethyl, propyl, isopropyl, n-butyl, 1-methylpropyl, 2-methylpropyl, n-pentyl, 1-methylbutyl, 2-methylbutyl, 3-methylbutyl, 1,2-dimethylpropyl, n-hexyl can be mentioned by way of example.

The $C_1$–$C_{30}$ alkyl groups A can be interrupted by 1–15 oxygen atoms and/or substituted with 1–10 hydroxy group, 1–5 alkoxy groups or 1–2 COOH groups, such as, e.g., $C_2H_4$—O—$CH_3$, $C_3H_6$—O—$CH_3$, $C_2H_4$—O—$(C_2H_4$—O$)_t$—$C_2H_4$—OH, $C_2H_4$—O—$(C_2H_4$—O$)_t$—$C_2H_4$—$OCH_3$ with t=0 to 13, $C_2H_4OH$, $C_3H_6OH$, $C_4H_8OH$, $C_5H_{10}OH$, $C_6H_{12}OH$, $C_7H_{14}OH$, as well as their branched isomers, $CH(OH)CH_2OH$, $CH(OH)CH(OH)CH_2OH$, $CH_2[CH(OH)]_uCH_2OH$, with u=1–10

$CH[CH_2(OH)]CH(OH)CH_2OH$, $C_2H_4CH(OH)CH_2OH$, $(CH_2)_sCOOH$ with s=1 to 15, $C_2H_4$—O—$(C_2H_4$—O$)_t$—$CH_2COOH$ with t=0 to 13, $C_2H_4$—O—$(C_2H_4$—O$)_t$—$C_2H_4$—$C_nF_{2n}X$ with t=0 to 13, n=4 to 20 and X=a flourine, chlorine, bromine or iodine atom.

Preferred meanings for A are hydrogen, $C_1$–$C_{10}$ alkyl, $C_2H_4$—O—$CH_3$, $C_3H_6$—O—$CH_3$, $C_2H_4$—O—$(C_2H_4$—O$)_x$—$C_2H_4$—OH, $C_2H_4$—O—$(C_2H_4$—O$)_x$—$C_2H_4$—$OCH_3$ with x=0 to 5, $C_2H_4OH$, $C_3H_6OH$, $CH_2[CH(OH)]_yCH_2OH$, with y=1–6

$CH[CH_2(OH)]CH(OH)CH_2OH$, $(CH_2)_wCOOH$ with w=1 to 10, $C_2H_4$—O—$(C_2H_4$—O$)_x$—$CH_2COOH$ with x=0 to 5, $C_2H_4$—O—$(C_2H_4$—O$)_x$—$C_2H_4$—$C_pF_{2p}X$ with x=0 to 5, p=4 to 15, and X=a fluorine atom.

If the compound of general formula I contains two radicals L—$R^F$, these radicals can be different from one another.

For radicals L, there can be mentioned by way of example, whereby α stands for the bond to the nitrogen atom and β stands for the bond to radical $R^F$:

α-$(CH_2)_k$-β with k=1–15

α-$CH_2$—$CH_2$—(O—$CH_2$—$CH_2$—$)_r$-β with r=1–6

α-$CH_2$—(O—$CH_2$—$CH_2$—$)_r$-β with r=1–6

α-$CH_2$—NH—CO-β

α-$CH_2$—$CH_2$—NH—$SO_2$-β

α-$CH_2$—NH—CO—$CH_2$—N($CH_2COOH$)—$SO_2$-β

α-$CH_2$—NH—CO—$CH_2$—N($C_2H_5$)—$SO_2$-β

α-$CH_2$—NH—CO—$CH_2$—N($C_{10}OH_{21}$)—$SO_2$-β

α-$CH_2$—NH—CO—$CH_2$—N($C_6H_{13}$)—$SO_2$-β

α-$CH_2$—NH—CO—$(CH_2)_{10}$—N($C_2H_5$)—$SO_2$-β

α-$CH_2$—NH—CO—$CH_2$—N(—$CH_2$—$C_6H_5$)—$SO_2$-β

α-$CH_2$—NH—CO—$CH_2$—N(—$CH_2$—$CH_2$—OH)$SO_2$-β

α-$CH_2$—NHCO—$(CH_2)_{10}$—S—$CH_2CH_2$-β

α-$CH_2NHCOCH_2$—O—$CH_2CH_2$-β

α-$CH_2$—$CH_2NHCOCH_2$—O—$CH_2CH_2$-β

α-$CH_2$—$(CH_2$—$CH_2$—O$)_r$—$(CH_2)_3NHCO$—$CH_2$—O—$CH_2CH_2$-β with r=1–6

α-$CH_2NHCO(CH_2)_{10}$—O—$CH_2CH_2$-β

α-$CH_2CH_2NHCO(CH_2)_{10}$—O—$CH_2CH_2$-β

α-$CH_2$—$C_6H_4$—O—$CH_2CH_2$-β whereby phenylene group 1,4 or 1,3 is linked

α-$CH_2$—O—$CH_2$—$C(CH_2$—$OCH_2CH_2$—$C_6F_{13})_2$—$CH_2$—$OCH_2$—$CH_2$-β

α-$CH_2$—$NHCOCH_2CH_2CON$—$CH_2CH_2NHCOCH_2N$($C_2H_5)SO_2C_8F_{17}$β

α-$CH_2$—$CH_2NHCOCH_2N(C_2H_5)$—$SO_2$-β

α-$CH_2$—O—$CH_2$—$CH(OC_{10}H_{21})$—$CH_2$—O—$CH_2CH_2$-β

α-$(CH_2NHCO)_4$—$CH_2O$—$CH_2CH_2$-β

α-$(CH_2NHCO)_3$—$CH_2O$—$CH_2CH_2$-β

α-$CH_2$—$OCH_2C(CH_2OH)_2$—$CH_2$—O—$CH_2CH_2$-β

$$\alpha\text{—}\underset{\underset{COOH}{|}}{C_6H_3}(\text{—O—})(\text{—}CH_2\text{—O—})\beta$$

α-$CH_2NHCOCH_2N(C_6H_5)$—$SO_2$-β

α-NHCO—$CH_2$—$CH_2$-β

α-NHCO—$CH_2$—O—$CH_2CH_2$-β

α-NH—CO-β

α-NH—CO—$CH_2$—N($CH_2COOH$)—$SO_2$-β

α-NH—CO—$CH_2$—N($C_2H_5$)—$SO_2$-β

α-NH—CO—$CH_2$—N($C_{10}H_{21}$)—$SO_2$-β

α-NH—CO—$CH_2$—N($C_6H_{13}$)—$SO_2$-62

α-NH—CO—$(CH_2)_{10}$—N($C_2H_5$)—$SO_2$-β

α-NH—CO—$CH_2$—N(—$CH_2$—$C_6H_5$)—$SO_2$-β

α-NH—CO—$CH_2$—N(—$CH_2$—$CH_2$—OH)$SO_2$-β

α-NH—CO—$CH_2$-β

α-$CH_2$—O—$C_6H_4$—O—$CH_2$—$CH_2$-β

α-$CH_2$—$C_6H_4$—O—$CH_2$—$CH_2$-β

α-N($C_2H_5$)—$SO_2$-β

α-N($C_6H_5$)—$SO_2$-β

α-N($C_{10}OH_{21}$)—$SO_2$-β

α-N($C_6H_{13}$)—$SO_2$-β

α-N($C_2H_4OH$)—$SO_2$-β

α-N($CH_2COOH$)—$SO_2$-β

α-N($CH_2C_6H_5$)—$SO_2$-β

α-N—[CH(CH$_2$OH)$_2$]—SO$_2$-β
α-N—[CH(CH$_2$OH)CH(OH)(CH$_2$OH)]—SO$_2$-β
Preferred:
α-CH$_2$—O—CH$_2$CH$_2$-β
α-CH$_2$—CH$_2$—(O—CH$_2$—CH$_2$—)$_y$-β with y=1–6
α-CH$_2$—(O—CH$_2$—CH$_2$—)$_y$-β with y=1–6
α-CH$_2$—CH$_2$—NH—SO$_2$-β Example 10
α-CH$_2$NHCOCH$_2$—O—CH$_2$CH$_2$-β
α-CH$_2$—CH$_2$NHCOCH$_2$—O—CH$_2$CH$_2$-β
α-CH$_2$—(CH$_2$—CH$_2$—O)$_y$—(CH$_2$)$_3$NHCO—CH$_2$—O—CH$_2$CH$_2$-β with y=1–6
α-CH$_2$NHCO(CH$_2$)$_{10}$—O—CH$_2$CH$_2$-β
α-CH$_2$CH$_2$NHCO(CH$_2$)$_{10}$—O—CH$_2$CH$_2$-β
α-CH$_2$—O—CH$_2$—CH(OC$_{10}$H$_{21}$)—CH$_2$—O—CH$_2$CH$_2$-β
α-CH$_2$—O—C$_6$H$_4$—O—CH$_2$—CH$_2$-β
α-CH$_2$-C$_6$H$_4$—O—CH$_2$—CH$_2$-β

Quite especially preferred according to the invention are radicals L of the compounds that are mentioned in the examples of the description of this invention.

For U, the above-indicated radicals for L, and the radicals that are identified as preferred and especially preferred, as well as the radicals that are mentioned above for the meaning of alkylene and that are optionally preferred and especially preferred hold true, provided that no α-position nitrogen atom and no terminal (β-position) SO$_2$ group or CO group need be present.

Preferred radicals B$^1$ are hydrogen, straight-chain or branched C$_1$–C$_{10}$ alkyl radicals, which are optionally interrupted by 1–5 oxygen atoms, and/or are optionally substituted with 1–5 hydroxy groups, 1–2 COOH groups, a phenyl group that is optionally substituted by a COOH group, a benzyl group and/or 1–5 OR$^4$ groups, with R$^4$ in the meaning of a hydrogen atom or a C$_1$–C$_3$ alkyl radical.

Preferred radicals R$_F$ are straight-chain or branched perfluorinated alkyl radicals of formula C$_p$F$_{2p}$X, whereby 4 is equal to or less than p and p is equal to or less than 15, and X stands for a terminal fluorine atom.

The production of the compounds of general formula I according to the invention $$K—N(A)—L—R^F \quad (I)$$

with

K in the meaning of a complexing agent or a metal complex of general formula II (II)

can be carried out according to the following processes:
Process A:
The carboxylic acid of formula III already contains metal ion equivalent R$^1$:

(III)

(IV)

(I)

Carboxylic acid III that is optionally activated in situ with R$^1$ in the meaning of a metal ion equivalent is reacted to an amide I with an amine IV in a coupling reaction.

This process for the production of metal complex carboxylic acid amides is known from DE 196 52 386.

The mixture of metal complex carboxylic acid III that is used in the coupling reaction, which optionally contains existing carboxy groups and/or hydroxy groups in protected form, and at least one solubilizing substance in an amount of up to 5, preferably 0.5–2 molar equivalents relative to the metal complex carboxylic acid, can be produced both in an upstream reaction stage and (e.g., by concentration by evaporation, freeze-drying or spray-drying of an aqueous or water-miscible solution of the components or by precipitation with an organic solvent from such a solution) are isolated and then are reacted in DMSO with a dehydrating reagent and optionally a coupling adjuvant and are formed in situ optionally by adding solubilizing substance(s) to the DMSO suspension from the metal complex carboxylic acid, dehydrating reagent and optionally a coupling adjuvant.

The reaction solution that is produced according to one of these processes is kept for pretreatment (acid activation) for 1 to 24, preferably 3 to 12 hours at temperatures of 0 to 50° C., preferably at room temperature.

Then, an amine of general formula IV (IV)

in which radicals R$^3$, L, R$^F$ and A have the above-indicated meanings, is added without solvent or dissolved, for example, to dimethyl sulfoxide, alcohols, such as, e.g., methanol, ethanol, isopropanol or mixtures thereof, formamide, dimethylformamide, water or mixtures of the indicated solvents, preferably in dimethyl sulfoxide, water or solvents that are mixed with water. For amide coupling, the reaction solution that is thus obtained is kept at temperatures of 0 to 70° C., preferably 30 to 60° C., for 1 to 48, preferably 8 to 24 hours.

In some cases, it has proven advantageous to use the amine in the form of its salts, e.g., as hydrobromide or hydrochloride in the reaction. To release the amine, a base such as, e.g., triethylamine, diisopropylethylamine, N-methylmorpholine, pyridine, tripropylamine, tributylamine, lithium hydroxide, lithium carbonate, sodium hydroxide or sodium carbonate is added.

The optionally still present protective groups are then cleaved off.

The reaction product is isolated according to the methods that are known to one skilled in the art, preferably by precipitation with organic solvents, preferably acetone, 2-butanone, diethyl ether, ethyl acetate, methyl-t-butyl ether, isopropanol or mixtures thereof. The additional purification can be carried out by, for example, chromatography, crystallization or ultrafiltration.

As solubilizing substances, alkali salts, alkaline-earth salts, trialkylammonium salts, tetraalkylammonium salts, ureas, N-hydroxyimides, hydroxyaryltriazoles, and substituted phenols and salts of heterocyclic amines are suitable. By way of example, there can be mentioned: lithium chloride, lithium bromide, lithium iodide, sodium bromide, sodium iodide, lithium methane sulfonate, sodium methane sulfonate, lithium-p-toluenesulfonate, sodium-p-toluenesulfonate, potassium bromide, potassium iodide, sodium chloride, magnesium bromide, magnesium chloride, magnesium iodide, tetraethylammonium-p-toluenesulfonate, tetramethylammonium-p-toluenesulfonate, pyridinium-p-toluenesulfonate, triethylammonium-p-toluenesulfonate, 2-morpholinoethylsulfonic acid, 4-nitrophenol, 3,5-dinitrophenol, 2,4-dichlorophenol, N-hydroxysuccinimide, N-hydroxyphthalimide, urea, tetramethylurea, N-methylpyrrolidone, formamide as well as cyclic ureas, whereby the first five mentioned are preferred.

As dehydrating reagents, all agents that are known to one skilled in the art are used. By way of example, there can be mentioned carbodiimide and onium reagents, such as, e.g., dicyclohexylcarbodiimide (DCCl), 1-ethyl-3-(3-dimethylaminopropyl)-carbodiimide-hydroxychloride (EDC), benzotriazol-1-yloxytris(dimethylamino)-phosphonium hexafluorophosphate (BOP) and O-(benzotriazol-1-yl)-1,1,3,3-tetramethyluronium hexafluorophosphate (HBTU), preferably DCCl.

In the literature, for example, the following suitable processes are described:

Aktivierung von Carbonsäuren. Übersicht in Houben-Weyl, Methoden der Organischen Chemie [Activation of Carboxylic Acids. Survey in Houben-Weyl, Methods of Organic Chemistry], Volume XV/2, Georg Thieme Verlag Stuttgart, 1974 (and J. Chem. Research (S) 1996, 302).

Aktivierung mit Carbodiimiden [Activation with Carbodiimides]. R. Schwyzer and H. Kappeler, Helv. 46: 1550 (1963).

E. Wünsch et al., Vol. 100: 173 (1967).

Aktivierung mit Carbodiimiden/Hydroxysuccinimid [Activation with Carbodiimides/Hydroxysuccinimide]: J. Am. Chem. Soc. 86: 1839 (1964) as well as J. Org. Chem. 53: 3583 (1988). Synthesis 453 (1972).

Anhydridmethode, 2-Ethoxy-1-ethoxycarbonyl-1,2-dihydrochinolin [Anhydride Methods, 2-Ethoxy-1-ethoxycarbonyl-1,2-dihydroquinoline]: B. Belleau et al., J. Am. Chem. Soc., 90: 1651 (1986), H. Kunz et al., Int. J. Pept. Prot. Res., 26: 493 (1985) and J. R. Voughn, Am. Soc. 73: 3547 (1951).

Imidazolid-Methode [Imidazolide Method]: B. F. Gisin, R. B. Menifield, D. C. Tosteon, Am. Soc. 91: 2691 (1969).

Säurechlorid-Methoden, Thionylchlorid [Acid Chloride Methods, Thionyl Chloride]: Helv., 42: 1653 (1959).

Oxalylchlorid [Oxalyl Chloride]: J. Org. Chem., 29: 843 (1964).

As coupling adjuvants that are optionally to be used, all that are known to one skilled in the art are suitable (Houben-Weyl, Methoden der organischen Chemie, Volume XV/2, Georg Thieme-Verlag, Stuttgart, 1974). By way of example, there can be mentioned 4-nitrophenol, N-hydroxysuccinimide, 1-hydroxybenzotriazole, 1-hydroxy-7-aza-benzotriazole, 3,5-dinitrophenol and pentafluorophenol. Preferred are 4-nitro-phenol and N-hydroxysuccinimide; especially preferred in this case is the first-mentioned reagent.

The cleavage of the protective groups is done according to the processes that are known to one skilled in the art, for example by hydrolysis, hydrogenolysis, alkaline saponification of esters with alkali in aqueous-alcoholic solution at temperatures of 0° to 50° C., acid saponification with mineral acids or in the case of, e.g., tert-butylesters with the aid of trifluoroacetic acid [Protective Groups in Organic Synthesis, 2nd Edition, T. W. Greene and P. G. M. Wuts, John Wiley and Sons, Inc. New York, 1991], in the case of benzyl ethers with hydrogen/palladium/carbon.

The production of the starting material, the compounds of formula III,

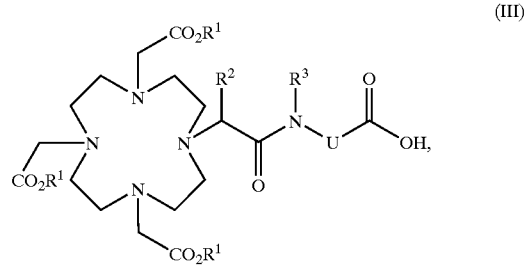

is known from DE 196 52 386.

The amines of general formula IV

are commercially available products (Fluorochem, ABCR) or can be obtained according to the following process from compounds of general formula V by reaction with an amine of general formula VI and subsequent reduction of compounds of general formula VII:

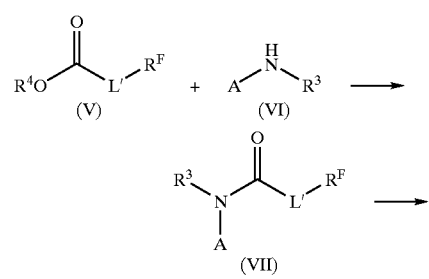

-continued

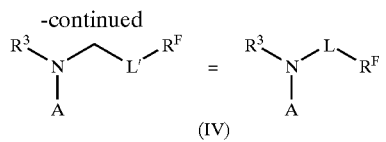

(IV)

in which
R^F, A, L and R³ have the above-mentioned meaning, and
L' has the meaning of group L, in which the α-CH₂ group is absent, and
R⁴ stands for hydrogen or a methyl group.

According to the process that is already described above for the activation of carboxylic acid III that is disclosed in the literature, acid V is activated before the reaction with amine VI. For R⁴ in the meaning of a methyl group, an aminolysis is carried out.

The compounds of general formula V are commercially available products (Fluorochem, ABCR) or are produced as disclosed in DE 196 03 033.

The compounds of formula VI are commercially available products (Fluorochem, ABCR) or can be produced as described in Houben-Weyl, Methoden der organischen Chemie, XI/2 Stickstoff-verbindungen [Nitrogen Compounds], Georg Thieme Verlag Stuttgart, 1957, p. 680; J. E. Rickman and T. Atkins, Am. Chem. Soc., 96:2268, 1974, 96: 2268; F. Chavez and A. D. Sherry, J. Org. Chem. 1989, 54: 2990.

The compounds of general formula IV are obtained in a way that is known in the art [Helv. Chim. Acta, 77: 23 (1994)] by reduction of the compounds of general formula VII, for example, with diborane or lithium aluminum hydride and cleavage of the protective groups.

Process B

As starting material, the carboxylic acid of formula IIIa with R¹ in the meaning of hydrogen is used—it does not contain any metal ion equivalent R¹. The carboxyl groups are protected according to the processes that are known to one skilled in the art, and a compound of formula IIIb is obtained, whereby R⁵ stands for any protective group.

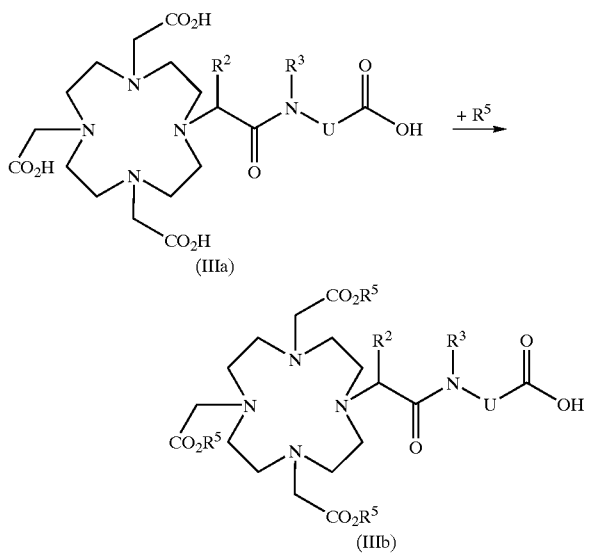

As carboxyl protective groups, e.g., straight-chain or branched C₁–C₆ alkyl, aryl and aralkyl groups, for example, the methyl, ethyl, propyl, butyl, phenyl, benzyl, diphenylmethyl, triphenylmethyl, bis(p-nitrophenyl)-methyl group as well as trialkylilyl groups are suitable. Prefered is the t-butyl group.

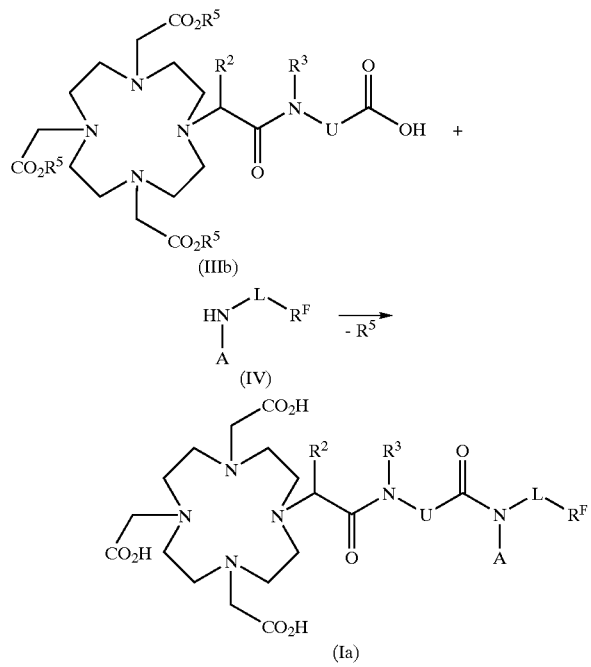

The reaction of protected carboxylic acid IIIb with the amine of formula IV and the cleavage of the protective groups is carried out as described under process A, and in a subsequent step, carboxylic acid Ia that is obtained is reacted with at least one metal oxide or metal salt of an element of the desired atomic number, as is disclosed in, e.g., DE 195 25 924.

If the metal complex that is obtained from process A or B contains free COOH groups, these groups can also be present as salts of physiologically compatible inorganic or organic bases.

The neutralization of optionally still present free carboxy groups is then carried out with the aid of inorganic bases (for example hydroxides, carbonates or bicarbonates) of, for example, sodium, potassium, lithium, magnesium or calcium and/or organic bases, such as, i.a., primary, secondary and tertiary amines, such as, for example, ethanolamine, morpholine, glucamine, N-methylglucamine and N,N-dimethylglucamine, as well as basic amino acids, such as, for example, lysine, arginine and ornithine or amides of originally neutral or acidic amino acids.

For the production of neutral complex compounds, enough of the desired bases can be added to, for example, the acid complex salts in aqueous solution or suspension so that the neutral point is reached. The solution that is obtained can then be evaporated to the dry state in a vacuum. It is frequently advantageous to precipitate the neutral salts that are formed by adding water-miscible solvents, such as, for example, lower alcohols (methanol, ethanol, isopropanol, etc.), lower ketones (acetone, etc.), polar ethers (tetrahydrofuran, dioxane, 1,2-dimethoxyethane, etc.) and thus to obtain easily isolated and readily purified crystallizates. It has proven especially advantageous to add the desired bases as early as during the complexing of the reaction mixture and thus to save a process step.

With the compounds according to the invention, higher blood concentrations are achieved than with extracellular contrast media. They are dispersed after i.v. administration only into the intravascular space, and they thus have a decisive advantage compared to the extracellular contrast media.

Better elimination from the blood via the kidneys ensures a small burden on the overall organism.

The compounds of this invention are distinguished by better compatibility, higher lymph node concentration in three successive lymph node stations (which is especially important for i.v. lymphography). They are thus especially well suited for use in MRT lymphography.

The compounds according to the invention are suitable for NMR diagnosis and x-ray diagnosis and for radiodiagnosis and radiotherapy.

The subject of the invention is therefore also the use of the compounds according to the invention for the production of a contrast medium for use in NMR diagnosis and x-ray diagnosis, for radiodiagnosis and radiotherapy.

Subjects of the invention are also pharmaceutical agents that contain at least one physiologically compatible compound of general formula I, optionally with the additives that are commonly used in galenicals.

The production of the pharmaceutical agents according to the invention is carried out in a way that is known in the art by the complex compounds according to the invention—optionally with the addition of the additives that are commonly used in galenicals—being suspended or dissolved in aqueous medium and then the suspension or solution optionally being sterilized. Suitable additives are, for example, physiologically harmless buffers (such as, for example, tromethamine), additives of complexing agents or weak complexes (such as, for example, diethylenetriaminepentaacetic acid or the Ca-complexes that correspond to the metal complexes according to the invention) or—if necessary—electrolytes such as, for example, sodium chloride or—if necessary—antioxidants, such as, for example, ascorbic acid.

If suspensions or solutions of the agents according to the invention in water or physiological hydrochloric acid solution are desired for enteral or parenteral administration or other purposes, they are mixed with one or more adjuvant(s) that are commonly used in galenicals [for example, methyl cellulose, lactose, mannitol] and/or surfactant(s) [for example, lecithins, Tween$^{(R)}$, Myrj$^{(R)}$] and/or flavoring substance(s) for taste correction [for example, ethereal oils].

Basically, it is also possible to produce the pharmaceutical agents according to the invention without isolating the complexes. In any case, special care must be used to carry out the chelation so that the complexes according to the invention are practically free of non-complexed metal ions that have a toxic effect.

This can be ensured, for example, with the aid of color indicators, such as xylenol orange, by control titrations during the production process. The invention therefore also relates to a process for the production of the complex compounds and their salts. As a final precaution, there remains purification of the isolated complex.

In the in-vivo administration of the agents according to the invention, the latter can be administered together with a suitable vehicle, such as, for example, serum or physiological common salt solution and together with another protein, such as, for example, human serum albumin (HSA).

The agents according to the invention are usually administered parenterally, preferably i.v. They can also be administered intravascularly or interstitially/intracutaneously depending on whether bodily vessels or tissue are to be studied.

The pharmaceutical agents according to the invention preferably contain 0.1 μmol–1 mol/l of the complex and are generally dosed in amounts of 0.0001–5 mmol/kg.

The examples below are used for a more detailed explanation of the subject of the invention, without intending that it be limited to these examples.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius; and, unless otherwise indicated, all parts and percentages are by weight.

The entire disclosure of all applications, patents and publications, cited above, and of corresponding German application No. 199 14 101.0, filed Mar. 22, 1999, and U.S. Provisional Application Serial No. 60/128,623, filed Apr. 9, 1999, are hereby incorporated by reference.

Figure 1:
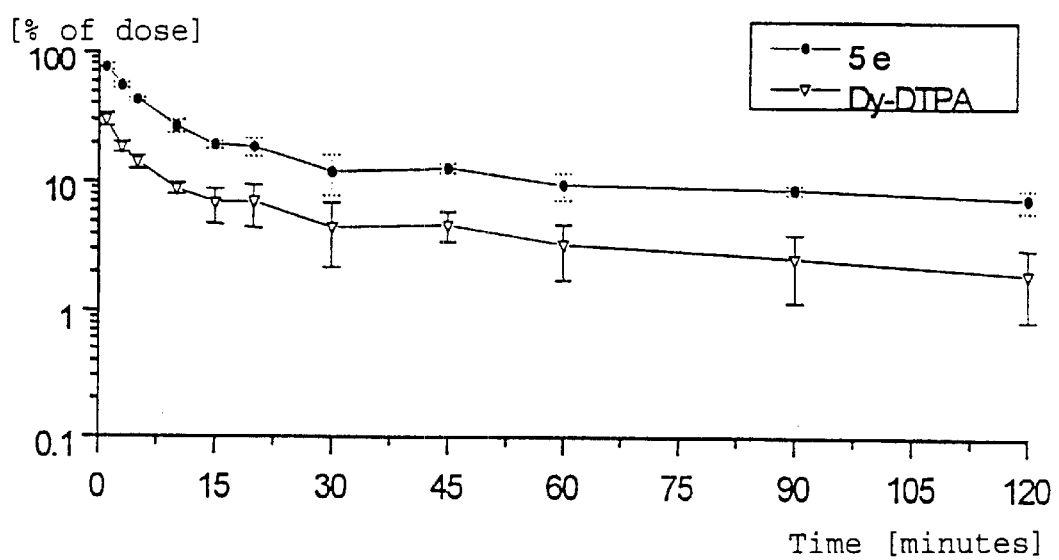
FIG. 1 shows the blood level (in % of the dose) of Gd (perfluoroalkyl-containing compound of Example 5e) and Dy (Dy-DTPA) after intravenous administration of 100 μmol/kg of body weight in rats in each case (n=3).

EXAMPLE 1 a) 2H,2H,4H,4H,5H,5H-3-Oxa-perfluorotridecanoic acid-N-(2-methoxy)-ethyl-amide 8.90 g (70 mmol) of oxalyl chloride is added to 30 g (57.45 mmol) of 2H,2H,4H,4H,5H,5H-3-oxa-perfluorotridecanoic acid in 300 ml of dichloromethane, and it is stirred for 12 hours at room temperature. It is evaporated to the dry state in a vacuum. The residue is dissolved in 100 ml of dichloromethane and added in drops at 0° C. to a solution of 4.51 g (60 mmol) of 2-methoxyethylamine and 6.07 g (60 mmol) of triethylamine, dissolved in 200 ml of dichloromethane. It is stirred for 3 hours at 0° C., then for 6 hours at room temperature. 300 ml of 5% aqueous hydrochloric acid is added, and it is thoroughly stirred for 15 minutes. The organic phase is separated, dried on magnesium sulfate and evaporated to the dry state in a vacuum. The residue is chromatographed on silica gel (mobile solvent: dichloromethane/acetone=20:1).

Yield: 30.28 g (91 of theory) of a colorless solid

Elementary analysis:

| Cld: | C 31.10 | H 2.44 | N 2.42 | F 55.76 |
|---|---|---|---|---|
| Fnd: | C 30.87 | H 2.58 | N 2.35 | F 55.51 | b) N-(2-Methoxyethyl)-N-(1H,1H,2H,2H,4H,4H,5H,5H-3-oxa)-perfluorotridecylamine 30 g (51.79 mmol) of the title compound of Example 1a is dissolved in 300 ml of tetrahydrofuran, and 31 ml of 10 M boranedimethyl sulfide (in tetrahydrofuran) is added. It is refluxed for 16 hours. It is cooled to 0° C., and 200 ml of methanol is added in drops, then it is evaporated to the dry state in a vacuum. The residue is taken up in a mixture of 300 ml of ethanol/50 ml of 10% aqueous hydrochloric acid, and it is stirred for 8 hours at 40° C. It is evaporated to the dry state in a vacuum, the residue is taken up in 300 ml of 5% aqueous sodium hydroxide solution, and it is extracted 3 times with 300 ml of dichloromethane each. The organic phases are dried on magnesium sulfate, evaporated to the dry state in a vacuum, and the residue is chromatographed on silica gel (mobile solvent: dichloromethane/2 propanol= 20:1).

Yield: 26.93 g (92% of theory) of a colorless solid
Elementary analysis (relative to anhydrous substance):

| Cld: | C 31.87 | H 2.85 | N 2.48 | F 57.14 |
|---|---|---|---|---|
| Fnd: | C 31.69 | H 3.10 | N 2.27 | F 56.88 | c) 1,4,7-Tris(carboxylatomethyl)-10-[(3-aza-4-oxo-hexan-5-ylic)-acid-N-(2-methoxyethyl)-N-(1H,1H,2H,2H,4H,4H,5H,5H-3-oxa)-perfluorotridecyl)-amide]-1,4,7,10-tetraazacyclododecane, gadolinium complex 10 g (15.88 mmol) of the gadolinium complex of 10-[1-(carboxymethylcarboamoyl)-ethyl]-1,4,7,10-tetraazacyclododecane-1,4,7-triacetic acid and 1.35 g (31.76 mmol) of lithium chloride are dissolved at 60° C. in 100 ml of dimethyl sulfoxide. It is cooled to 15° C., and 8.98 (15.88 mmol) of the title compound of Example 1b is added. It is stirred for 10 minutes, and then 7.42 g (30 mmol) of 2-ethoxy-1-ethoxycarbonyl-1,2-dihydroquinoline is added. It is stirred for 12 hours at room temperature. The solution is poured into a mixture of 200 ml of acetone/1300 ml of diethyl ether, and it is stirred for 2 hours at room temperature. The deposited precipitate is filtered off, and is dissolved in a mixture of a little ethanol/water and chromatographed on silica gel RP-18 (mobile solvent: gradient that consists of tetrahydrofuran/acetonitrile/water).

Yield: 15.14 g (81% of theory) of a colorless, amorphous powder
Water content: 5.7%
Elementary analysis (relative to anhydrous substance):

| Cld: | C 34.70 | H 3.77 | N 7.14 | F 27.44 | Gd 13.16 |
|---|---|---|---|---|---|
| Fnd: | C 34.51 | H 3.94 | N 7.02 | F 27.25 | Gd 13.18 |

EXAMPLE 2 a) 2H,2H,4H,4H,5H,5H-3-Oxa)-perfluorotridecanoic acid-N-(2,3-dihydroxypropyl)-amide 8.90 g (70 mmol) of oxalyl chloride is added to 30 g (57.45 mmol) of 2H,2H,4H,4H,5H,5H-3-oxa-perfluorotridecanoic acid in 300 ml of dichloromethane, and it is stirred for 12 hours at room temperature. It is evaporated to the dry state in a vacuum. The residue is dissolved in 100 ml of dichloromethane and added in drops at 0° C. to a solution of 5.47 g (60 mmol) of 2,3-dihydroxypropylamine and 6.07 g (60 mmol) of triethylamine, dissolved in 200 ml of dichloromethane. It is stirred for 3 hours at 0° C., then for 6 hours at room temperature. 300 ml of 5% aqueous hydrochloric acid is added, and it is thoroughly stirred for 15 minutes. The organic phase is separated, dried on magnesium sulfate and evaporated to the dry state in a vacuum. The residue is chromatographed on silica gel (mobile solvent: dichloromethane/ethanol=15:1).

Yield: 29.70 g (87% of theory) of a colorless solid
Elementary analysis:

| Cld: | C 30.32 | H 2.20 | N 2.36 | F 54.35 |
|---|---|---|---|---|
| Fnd: | C 30.12 | H 2.41 | N 2.18 | F 54.15 | b) N-(2,3-Dihydroxypropyl)-N-(1H,1H,2H,2H,4H,4H,5H,5H-3-oxa-perfluoro-tridecyl)-amine 30 g (48.8 mmol) of the title compound of Example 2a is dissolved in 300 ml of tetrahydrofuran, and 50 ml of 10 M boranedimethyl sulfide (in tetrahydrofuran) is added. It is refluxed for 16 hours. It is cooled to 0° C., and 300 ml of methanol is added in drops, and then it is evaporated to the dry state in a vacuum. The residue is taken up in a mixture of 300 ml of ethanol/50 ml of 10% aqueous hydrochloric acid, and it is stirred for 8 hours at 60° C. It is evaporated to the dry state in a vacuum, the residue is taken up in 300 ml of 5% aqueous sodium hydroxide solution, and it is extracted 3 times with 300 ml of dichloromethane each. The organic phases are dried on magnesium sulfate, evaporated to the dry state in a vacuum, and the residue is chromatographed on silica gel (mobile solvent: dichloromethane/methanol=15:1).

Yield: 24.07 g (85% of theory) of a colorless solid
Elementary analysis:

| Cld: | C 31.05 | H 2.61 | N 2.41 | F 55.66 |
|---|---|---|---|---|
| Fnd: | C 31.91 | H 2.78 | N 2.33 | F 55.47 | c) 1,4,7-Tris(carboxylatomethyl)-10-[(3-aza-4-oxo-hexan-5-ylic)-acid-N-(2,3-dihydroxypropyl)-N-(1H,1H,2H,2H,4H,4H,5H,5H-3-oxa)-perfluorotridecyl)-amide]-1,4,7,10-tetraazacyclododecane, gadolinium complex 10 g (15.88 mmol) of the gadolinium complex of 10-[1-(carboxymethylcarboamoyl)-ethyl]-1,4,7,10-tetraazacyclododecane-1,4,7-triacetic acid and 1.35 g (31.76 mmol) of lithium chloride are dissolved at 60° C. in 100 ml of dimethyl sulfoxide. It is cooled to 15° C., and 9.21 (15.88 mmol) of the title compound of Example 2b is added. It is stirred for 10 minutes, and then 7.42 g (30 mmol) of 2-ethoxy-1-ethoxycarbonyl-1,2-dihydroquinoline is added. It is stirred for 12 hours at room temperature. The solution is poured into a mixture of 200 ml of acetone/1300 ml of diethyl ether, and it is stirred for 2 hours at room temperature. The deposited precipitate is filtered off, dissolved in a mixture that consists of a little ethanol/water and chromatographed on silica gel RP-18 (mobile solvent: gradient that consists of tetrahydrofuran/acetonitrile/water).

Yield: 16.09 g (85% of theory) of a colorless, amorphous powder
Water content: 6.3%
Elementary analysis (relative to anhydrous substance):

| Cld: | C 34.26 | H 3.64 | N 7.05 | F 27.10 | Gd 13.19 |
|---|---|---|---|---|---|
| Fnd: | C 34.12 | H 3.38 | N 6.91 | F 26.88 | Gd 12.93 |

EXAMPLE 3 a) 2H,2H,4H,4H,5H,5H-3-Oxa-perfluorotridecanoic acid-N-(5-hydroxy-3-oxa-pentyl)-amide 8.90 g (70 mmol) of oxalyl chloride is added to 30 g (57.45 mmol) of 2H,2H,4H,4H,5H,5H-3-oxa-perfluorotridecanoic acid in 300 ml of dichloromethane, and it is stirred for 12 hours at room temperature. It is evaporated to the dry state in a vacuum. The residue is dissolved in 100 ml of dichloromethane and added in drops at 0° C. to a solution of 6.25 g (60 mmol) of 5-hydroxy-3-oxa-pentylamine and 6.07 g (60 mmol) of triethylamine, dissolved in 200 ml of dichloromethane. It is stirred for 3 hours at 0° C., then for 6 hours at room temperature. 300 ml of 5% aqueous hydrochloric acid is added, and it is thoroughly stirred for 15 minutes. The organic phase is separated, dried on magnesium sulfate and evaporated to the dry state in a vacuum. The residue is chromatographed on silica gel (mobile solvent: dichloromethane/acetone=15:1).

Yield: 32.20 g (92% of theory) of a colorless solid
Elementary analysis:

| Cld: | C 31.54 | H 2.65 | N 2.30 | F 53.01 |
|---|---|---|---|---|
| Fnd: | C 31.61 | H 2.84 | N 2.14 | F 52.85 | b) N-(5-Hydroxy-3-oxa-pentyl)-N-(1H,1H,2H,2H,4H,4H,5H,5H-3-oxa-perfluorotridecyl)-amine 30 g (49.24 mmol) of the title compound of Example 3a is dissolved in 300 ml of tetrahydrofuran, and 31 ml of 10 M boranedimethyl sulfide (in tetrahydrofuran) is added. It is refluxed for 16 hours. It is cooled to 0° C., and 200 ml of methanol is added in drops, and then it is evaporated to the dry state in a vacuum. The residue is taken up in a mixture that consists of 300 ml of ethanol/50 ml of 10% aqueous hydrochloric acid, and it is stirred for 10 hours at 50° C. It is evaporated to the dry state in a vacuum, the residue is taken up in 300 ml of 5% aqueous sodium hydroxide solution, and it is extracted 3 times with 300 ml of dichloromethane each. The organic phases are dried on magnesium sulfate, evaporated to the dry state in a vacuum, and the residue is chromatographed on silica gel (mobile solvent: dichloromethane/2-propanol=20:1).

Yield: 26.09 g (89% of theory) of a colorless solid
Elementary analysis:

| Cld: | C 32.28 | H 3.05 | N 2.35 | F 54.25 |
|---|---|---|---|---|
| Fnd: | C 32.12 | H 3.21 | N 2.18 | F 54.09 | c) 1,4,7-Tris(carboxylatomethyl)-10-[(3-aza-4-oxo-hexan-5-ylic)-acid-N-(5-hydroxy-3-oxa-pentyl)-N-(1H,1H,2H,2H,4H,4H,5H,5H-3-oxa)-perfluorotridecyl)-amide]-1,4,7,10-tetraazacyclododecane, gadolinium complex 10 g (15.88 mmol) of the gadolinium complex of 10-[1-(carboxymethylcarboamoyl)-ethyl]-1,4,7,10-tetraazacyclododecane-1,4,7-triacetic acid and 1.35 g (31.76 mmol) of lithium chloride are dissolved at 60° C. in 100 ml of dimethyl sulfoxide. It is cooled to 15° C., and 9.45 (15.88 mmol) of the title compound of Example 3b is added. It is stirred for 10 minutes, and then 7.42 g (30 mmol) of 2-ethoxy-1-ethoxycarbonyl-1,2-dihydroquinoline is added. It is stirred for 12 hours at room temperature. The solution is poured into a mixture that consists of 200 ml of acetone/1300 ml of diethyl ether, and it is stirred for 2 hours at room temperature. The deposited precipitate is filtered off, dissolved in a mixture that consists of a little ethanol/water and chromatographed on silica gel RP-18 (mobile solvent: gradient that consists of tetrahydrofuran/acetonitrile/water).

Yield: 16.10 g (84% of theory) of a colorless, amorphous powder
Water content: 5.7%
Elementary analysis (relative to anhydrous substance):

| Cld: | C 34.83 | H 3.84 | N 6.96 | F 26.76 | Gd 13.03 |
|---|---|---|---|---|---|
| Fnd: | C 34.65 | H 3.96 | N 6.84 | F 26.62 | Gd 12.91 |

EXAMPLE 4 a) 2H,2H,4H,4H,5H,5H-3-Oxa-perfluorotridecanoic acid-N-(2-hydroxyethyl)-amide 8.90 g (70 mmol) of oxalyl chloride is added to 30 g (57.45 mmol) of 2H,2H,4H,4H,5H,5H-3-oxa-perfluorotridecanoic acid in 300 ml of dichloromethane, and it is stirred for 12 hours at room temperature. It is evaporated to the dry state in a vacuum. The residue is dissolved in 100 ml of dichloromethane and added in drops at 0° C. to a solution of 3.66 g (60 mmol) of 2-aminoethanol and 6.07 g (60 mmol) of triethylamine, dissolved in 200 ml of dichloromethane. It is stirred for 3 hours at 0° C., then for 6 hours at room temperature. 300 ml of 5% aqueous hydrochloric acid is added, and it is thoroughly stirred for 15 minutes. The organic phase is separated, dried on magnesium sulfate and evaporated to the dry state in a vacuum. The residue is chromatographed on silica gel (mobile solvent: dichloromethane/acetone=20:1).

Yield: 28.90 g (89% of theory)
Elementary analysis:

| Cld: | C 29.75 | H 2.14 | N 2.48 | F 57.14 |
|---|---|---|---|---|
| Fnd: | C 29.61 | H 2.29 | N 2.37 | F 57.01 | b) N-(2-Hydroxyethyl)-N-(1H,1H,2H,2H,4H,4H,5H,5H-3-oxa)-perfluorotridecyl)-amine 28 g (49.54 mmol) of the title compound of Example 4a is dissolved in 300 ml of tetrahydrofuran, and 31 ml of 10 M boranedimethyl sulfide (in tetrahydrofuran) is added. It is refluxed for 16 hours. It is cooled to 0° C., and 200 ml of methanol is added in drops, then it is evaporated to the dry state in a vacuum. The residue is taken up in a mixture that consists of 300 ml of ethanol/50 ml of 10% aqueous hydrochloric acid, and it is stirred for 10 hours at 50° C. It is evaporated to the dry state in a vacuum, the residue is taken up in 300 ml of 5% aqueous sodium hydroxide solution, and it is extracted 3 times with 300 ml of dichloromethane each. The organic phases are dried on magnesium sulfate, evaporated to the dry state in a vacuum, and the residue is chromatographed on silica gel (mobile solvent: dichloromethane/2 propanol=15:1).

Yield: 25.12 g (92% of theory) of a colorless solid
Elementary analysis (relative to anhydrous substance):

| Cld: | C 30.50 | H 2.56 | N 2.54 | F 58.59 |
|---|---|---|---|---|
| Fnd: | C 30.32 | H 2.71 | N 2.48 | F 58.43 | c) 1,4,7-Tris(carboxylatomethyl)-10-[(3-aza-4-oxo-hexan-5-ylic)-acid-N-(2-hydroxyethyl)-N-(1H,1H,2H,2H,4H,4H,5H,5H-3-oxa)-perfluorotridecyl)-amine-amide]-1,4,7,10-tetraazacyclododecane, gadinium complex 10 g (15.88 mmol) of the gadolinium complex of 10-[1-(carboxymethylcarboamoyl)-ethyl]-1,4,7,10-tetraazacyclododecane-1,4,7-triacetic acid and 1.35 g (31.76 mmol) of lithium chloride are dissolved at 60° C. in 100 ml of dimethyl sulfoxide. It is cooled to 15° C., and 8.75 g (15.88 mmol) of the title compound of Example 4b is added. It is stirred for 10 minutes, and then 7.42 g (30 mmol) of 2-ethoxy-1-ethoxycarbonyl-1,2-dihydroquinoline is added. It is stirred for 12 hours at room temperature. The solution is poured into a mixture that consists of 200 ml of acetone/1300 ml of diethyl ether, and it is stirred for 2 hours at room temperature. The deposited precipitate is filtered off, dissolved in a mixture that consists of a little ethanol/water and chromatographed on silica gel RP-18 (mobile solvent: gradient that consists of tetrahydrofuran/acetonitrile/water).

Yield: 16.81 g (91% of theory) of a colorless, amorphous powder
Water content: 7.2%
Elementary analysis (relative to anhydrous substance):

| Cld: | C 34.08 | H 3.64 | N 7.23 | F 27.77 | Gd 13.52 |
|---|---|---|---|---|---|
| Fnd: | C 33.91 | H 3.82 | N 7.14 | F 27.58 | Gd 13.41 |

EXAMPLE 5 a) 2H,2H,4H,4H,5H,5H-3-Oxa-perfluorotridecanoic acid amide 8.90 g (70 mmol) of oxalyl chloride is added to 30 g (57.45 mmol) of 2H,2H,4H,4H,5H,5H-3-oxa-perfluorotridecanoic acid in 300 ml of dichloromethane, and it is stirred for 12 hours at room temperature. It is evaporated to the dry state in a vacuum. The residue is dissolved in 200 ml of dichloromethane. Then, ammonia gas is fed into the solution at 0° C. for about 2 hours. It is stirred for 4 more hours at 0° C., then for 2 hours at room temperature. 300 ml of 5% aqueous hydrochloric acid is added, and it is thoroughly stirred for 15 minutes. The organic phase is separated, dried on magnesium sulfate and evaporated to the dry state in a vacuum. The residue is chromatographed on silica gel (mobile solvent: dichloromethane/acetone=20:1).

yield: 27.85 g (93% of theory)
Elementary analysis:

| Cld: | C 27.66 | H 1.55 | N 2.69 | F 61.97 |
|---|---|---|---|---|
| Fnd: | C 27.49 | H 1.72 | N 2.54 | F 61.81 | b) 1H,1H,2H,2H,4H,4H,5H,5H-3-Oxa-perfluorotridecylamine, hydrochloride 27 g (51.8 mmol) of the title compound of Example 5a is dissolved in 300 ml of tetrahydrofuran, and 31 ml of 10 M boranedimethyl sulfide (in tetrahydrofuran) is added. It is refluxed for 16 hours. It is cooled to 0° C., and 200 ml of methanol is added in drops, then it is evaporated to the dry state in a vacuum. The residue is taken up in a mixture that consists of 400 ml of ethanol/100 ml of 10% aqueous hydrochloric acid, and it is stirred for 8 hours at 60° C. It is evaporated to the dry state in a vacuum, and the residue from a little ethanol/diethyl ether is recrystallized.

Yield: 26.75 g (95% of theory) of a colorless, crystalline solid
Elementary analysis:

| Cld: | C 26.51 | H 2.04 | N 2.58 | F 59.41 | Cl 6.52 |
|---|---|---|---|---|---|
| Fnd: | C 26.37 | H 2.21 | N 2.46 | F 59.25 | Cl 6.38 | c) 3,6,9,12,15-Pentaoxahexadecanoic acid-N-(1H,1H,2H,2H,4H,4H,5H,5H-3-oxa)-perfluorotridecyl)-amide 14.24 g (50 mmol) of 3,6,9,12,15-pentaoxahexadecanoic acid chloride is added in drops to 26.5 g (48.74 mmol) of the title compound of Example 5b and 14.8 g (146.2 mmol) of triethylamine, dissolved in 300 ml of dichloromethane, at 0° C., and it is stirred for 3 hours at 0° C. 300 ml of 5% aqueous hydrochloric acid is added, and it is thoroughly stirred for 30 minutes. The organic phase is separated, dried on magnesium sulfate and evaporated to the dry state in a vacuum. The residue is chromatographed on silica gel (mobile solvent: dichloromethane/acetone: 20:1).

Yield: 32.03 g (87% of theory) of a colorless oil
Elementary analysis:

| Cld: | C 36.57 | H 4.00 | N 1.85 | F 42.75 |
|---|---|---|---|---|
| Fnd: | C 36.46 | H 4.12 | N 1.76 | F 42.53 | d) N-(3,6,9,12,15-Pentaoxahexadecyl)-N-(1H,1H,2H,2H,4H,4H,5H,5H-3-oxa)-perfluorotridecyl)-amine 31 g (41.03 mmol) of the title compound of Example 5c is dissolved in 300 ml of tetrahydrofuran, and 25 ml of 10 M boranedimethyl sulfide (in tetrahydrofuran) is added. It is refluxed for 16 hours. It is cooled to 0° C., and 200 ml of methanol is added in drops, then it is evaporated to the dry state in a vacuum. The residue is taken up in a mixture that consists of 300 ml of ethanol/50 ml of 10% aqueous hydrochloric acid, and it is stirred for 8 hours at 40° C. It is evaporated to the dry state in a vacuum, the residue is taken up in 300 ml of 5% aqueous sodium hydroxide solution, and it is extracted 3 times with 300 ml of dichloromethane each. The organic phases are dried on magnesium sulfate, evaporated to the dry state in a vacuum, and the residue is chromatographed on silica gel (mobile solvent: dichloromethane/2 propanol=15:1).

Yield: 27.68kg (91% of theory)
Elementary analysis:

| Cld: | C 37.26 | H 4.35 | N 1.89 | F 43.56 |
|---|---|---|---|---|
| Fnd: | C 37.11 | H 4.51 | N 1.73 | F 43.41 | e) 1,4,7-Tris(carboxylatomethyl)-10-{(3-aza-4-oxo-hexan-5-ylic)-acid-[N-3,6,9,12,15-pentaoxa)-hexadecyl)-N-(1H,1H,2H,2H,4H,4H,5H,5H-3-oxa)-perfluorotridecyl]-amide}-1,4,7,10-tetraazacyclododecane, gadolinium complex 10 g (15.88 mmol) of the gadolinium complex of 10-[1-(carboxymethylcarboamoyl)-ethyl]-1,4,7,10-tetraazacyclododecane-1,4,7-triacetic acid and 1.35 g (31.76 mmol) of lithium chloride are dissolved at 60° C. in 100 ml of dimethyl sulfoxide. It is cooled to 15° C., and 11.77 (15.88 mmol) of the title compound of Example 5d is added. It is stirred for 10 minutes, and then 7.42 g (30 mmol) of 2-ethoxy-1-ethoxycarbonyl-1,2-dihydroquinoline is added. It is stirred for 12 hours at room temperature. The solution is poured into a mixture that consists of 200 ml of acetone/1300 ml of diethyl ether, and it is stirred for 2 hours at room temperature. The deposited precipitate is filtered off, dissolved in a mixture that consists of a little ethanol/water and chromatographed on silica gel RP-18 (mobile solvent: gradient that consists of tetrahydrofuran/acetonitrile/water).

Yield: 18.05 g (84% of theory) of a colorless, amorphous powder
Water content: 6.2%
Elementary analysis (relative to anhydrous substance):

| Cld: | C 37.28 | H 4.47 | N 6.21 | F 23.87 | Gd 11.62 |
|---|---|---|---|---|---|
| Fnd: | C 37.11 | H 4.61 | N 6.03 | F 23.64 | Gd 11.42 |

EXAMPLE 6 a) 1,4,7-Tris(carboxylatomethyl)-10-[(3-aza-4-oxo-hexan-5-ylic)-acid-N-(13-amino-4,7,13-trioxa-decyl)-amide]-1,4,7,10-tetraazacyclododecane, gadolinium complex 10 g (15.88 mmol) of the gadolinium complex of 10-[1-(carboxymethylcarboamoyl)-ethyl]-1,4,7,10-tetraazacyclododecane-1,4,7-triacetic acid and 1.35 g (31.76 mmol) of lithium chloride and 3.66 g (31.76 mmol) of N-hydroxysuccinimide are dissolved at 60° C. in 100 ml of dimethyl sulfoxide. It is cooled to 15° C., and 3.51 (17 mmol) of N,N'-dicyclohexylcarbodiimide is added and stirred for 5 hours at 15° C. To separate the urea, the solution is filtered. 14.66 g (60 mmol) of 1,13-diamino-4,7,13-trioxadecane and 2.02 g (20 mmol) of triethylamine are added to the filtrate, and it is stirred for 12 hours at room temperature. The solution is poured into 1500 ml of diethyl ether/50 ml of n-butanol, and it is stirred for 30 minutes. The precipitated solid is filtered off and chromatographed on silica gel RP-18 (mobile solvent: gradient that consists of tetrahydrofuran/acetonitrile/water).

Yield: 12.66 g (69% of theory) of a colorless, amorphous powder
Water content; 3.5%
Elementary analysis (relative to anhydrous substance):

| Cld: | C 30.16 | H 4.54 | N 8.49 | F 27.96 | Gd 13.61 |
|---|---|---|---|---|---|
| Fnd: | C 30.02 | H 4.68 | N 8.35 | F 27.81 | Gd 13.45 | b) 1,4,7-Tris(carboxylatomethyl)-10-{(3-aza-4-oxo-hexan-5-ylic)-acid- [N-4,7,10,17-tetraoxa-14-aza-17-oxo-$C_{20}$–$C_{28}$-hepta-decafluoro)-heptacosyl]-amide}-1,4,7,10-tetraazacyclododecane, gadolinium complex 11.3 g (21.64 mmol) of 2H,2H,4H,4H,5H,5H-3-oxa-perfluorotridecanoic acid, 0.85 g (20 mmol) of lithium chloride and 4.95 g (43 mmol) of N-hydroxysuccinimide are dissolved at 25° C. in 150 ml of dimethyl sulfoxide. It is cooled to 15° C., and 6.19 (30 mmol) of N,N'-dicyclohexylcarbodiimide is added and stirred for 5 hours at 15° C. To separate the urea, the solution is filtered. 12.5 g (10.82 mmol) of the title compound of Example 6a and 3.29 g (32.47 mmol) of triethylamine are added to the filtrate, and it is stirred for 12 hours at room temperature. The solution is poured into 1300 ml of diethyl ether/100 ml of acetone, and it is stirred for 30 minutes. The precipitated solid is filtered off and chromatographed on silica gel RP-18 (mobile solvent: gradient that consists of tetrahydrofuran/acetonitrile/water).

Yield: 13.01 g (90% of theory)
Water content: 6.7%
Elementary analysis (relative to anhydrous substance):

| Cld: | C 36.86 | H 4.30 | N 7.34 | F 24.17 | Gd 11.77 |
|---|---|---|---|---|---|
| Fnd: | C 36.68 | H 4.41 | N 7.25 | F 24.03 | Gd 11.55 |

EXAMPLE 7

1,4,7-Tris(carboxylatomethyl)-10-[-(3-aza-4-oxo-hexan-5-ylic)-acid-N-(1H,1H,2H,2H,4H,4H,5H,5H-3-oxa-perfluorotridecyl)-amide]-1,4,7, 10-tetraaza-cyclododecane, gadolinium complex 10 g (15.88 mmol) of the gadolinium complex of 10-[-1-(carboxymethylcarboamoyl)-ethyl]-1,4,7,10-tetraazacyclododecane-1,4,7-triacetic acid and 1.35 g (31.76 mmol) of lithium chloride and 3.66 g (31.76 mmol) of N-hydroxysuccinimide are dissolved at 60° C. in 100 ml of dimethyl sulfoxide. It is cooled to 15° C., and 3.51 (17 mmol) of N,N'-dicyclohexylcarbodiimide is added and stirred for 5 hours at 15° C. To separate the urea, the solution is filtered. 8.63 g (15.88 mmol) of the title compound of Example 5b and 5.06 g (50 mmol) of triethylamine are added to the filtrate, and it is stirred for 12 hours at room temperature. The solution is poured into 1500 ml of diethyl ether/100 ml of acetone, and it is stirred for 30 minutes. The precipitated solid is filtered off and chromatographed on silica gel RP-18 (mobile solvent: gradient that consists of tetrahydrofuran/acetonitrile/water).

Yield: 13.86 g (78% of theory) of a colorless, amorphous powder
Water content: 9.3%
Elementary analysis (relative to anhydrous substance):

| Cld: | C 33.28 | H 3.42 | N 7.51 | F 28.87 | Gd 14.05 |
|---|---|---|---|---|---|
| Fnd: | C 33.12 | H 3.61 | N 7.37 | F 28.69 | Gd 13.89 |

EXAMPLE 8 a) 2H,2H,4H,4H,5H,5H-3-Oxa-perfluorotridecanoic acid-N-(2,3,4,5,6-pentahydroxy)-hexylamide 8.90 g (70 mmol) of oxalyl chloride is added to 30 g (57.45 mmol) of 2H,2H,4H,4H,5H,5H-3-oxa-perfluorotridecanoic acid in 300 ml of dichloromethane, and it is stirred for 12 hours at room temperature. It is evaporated to the dry state in a vacuum. The residue is dissolved in 100 ml of dichloromethane and added in drops at 0° C. to a solution that consists of 10.87 (60 mmol) of glucamine and 6.07 g (60 mmol) of triethylamine, dissolved in 150 ml of dichloromethane/150 of dioxane. It is stirred for 3 hours at 0° C., then for 8 hours at room temperature. 400 ml of 5% aqueous hydrochloric acid is added, and it is thoroughly stirred for 15 minutes. The organic phase is separated, dried on magnesium sulfate and evaporated to the dry state in a vacuum. The residue is chromatographed on silica gel (mobile solvent: dichloromethane/methanol=5:1).

Yield: 30.71 g (78% of theory)
Elementary analysis:

| Cld: | C 31.55 | H 2.94 | N 2.04 | F 47.13 |
|---|---|---|---|---|
| Fnd: | C 31.44 | H 3.09 | N 1.97 | F 47.01 | b) N-(2,3,4,5,6-pentahydroxyhexyl)-N-1H,1H,2H,2H,4H,4H,5H,5H-3-oxa-perfluorotridecyl)-amine 30 g (43.77 mmol) of the title compound of Example 8a is dissolved in 300 ml of tetrahydrofuran, and 50 ml of 10 M boranedimethyl sulfide (in tetrahydrofuran) is added. It is refluxed for 48 hours. It is cooled to 0° C., and 500 ml of methanol is added in drops, then it is evaporated to the dry state in a vacuum. The residue is taken up in a mixture that consists of 500 ml of ethanol/100 ml of 10% aqueous hydrochloric acid, and it is stirred for 15 hours at 60° C. It is evaporated to the dry state in a vacuum, the residue is taken up in 400 ml of 5% aqueous sodium hydroxide solution and extracted 5 times each with 400 ml of chloroform. The organic phases are dried on magnesium sulfate, evaporated to the dry state in a vacuum, and the residue is chromatographed on silica gel (mobile solvent: dichloromethane/methanol=3:1).

Yield: 19.69 g (67% of theory) of a colorless solid
Elementary analysis:

| Cld: | C 32.20 | H 3.30 | N 2.09 | F 48.11 |
|---|---|---|---|---|
| Fnd: | C 32.05 | H 3.43 | N 1.97 | F 47.93 | c) 1,4,7-Tris(carboxylatomethyl)-10-{(3-aza-4-oxo-hexan-5-ylic)-acid-[N-2,3,5,6-pentahydroxy)-hexyl-N-(1H,1H,2H,2H,4H,4H,5H,5H-3-oxa-perfluorotridecyl]-amide}-1,4,7, 10-tetraazacyclododecane, gadolinium complex 10 g (15.88 mmol) of the gadolinium complex of 10-[1-(carboxymethylcarboamoyl)-ethyl]-1,4,7,10- tetraazacyclododecane-1,4,7-triacetic acid and 1.35 g (31.76 mmol) of lithium chloride are dissolved at 60° C. in 100 ml of dimethyl sulfoxide. It is cooled to 15° C., and 15.88 (15.88 mmol) of the title compound of Example 8b is added. It is stirred for 10 minutes, and then 7.42 g (30 mmol) of 2-ethoxy-1-ethoxycarbonyl-1,2-dihydroquinoline is added. It is stirred for 12 hours at room temperature. The solution is poured into a mixture that consists of 200 ml of acetone/ 1300 ml of diethyl ether, and it is stirred for 2 hours at room temperature. The deposited precipitate is filtered off, dissolved in a mixture that consists of a little ethanol/water and chromatographed on silica gel RP-18 (mobile solvent: gradient that consists of tetrahydrofuran/acetonitrile/water).

Yield: 16.10 g (79% of theory) of a colorless, amorphous powder

Water content: 6.3%

Elementary analysis (relative to anhydrous substance):

| Cld: | C 36.64 | H 3.93 | N 6.55 | F 25.17 | Gd 12.26 |
|---|---|---|---|---|---|
| Fnd: | C 34.49 | H 4.13 | N 6.48 | F 25.03 | Gd 12.11 |

EXAMPLE 9 a) 2H,2H,4H,4H,5H,5H-3-Oxa-perfluorotridecanoic acid-N-(2,2-dimethyl-5-hydroxy-1,3-dioxepan-6-yl)-amide 8.90 g (70 mmol) of oxalyl chloride is added to 30 g (57.45 mmol) of 2H,2H,4H,4H,5H,5H-3-oxa-perfluorotridecanoic acid in 300 ml of dichloromethane, and it is stirred for 12 hours at room temperature. It is evaporated to the dry state in a vacuum. The residue is dissolved in 100 ml of dichloromethane and added in drops at 0° C. to a solution that consists of 9.67 (60 mmol) of 5-amino-2,2-dimethyl-1,3-dioxepan-6-ol and 6.07 g (60 mmol) of triethylamine, dissolved in 200 ml of dichloromethane. It is stirred for 3 hours at 0° C., then for 5 hours at room temperature. 300 ml of water is added, and it is thoroughly stirred for 15 minutes. The organic phase is separated, dried on magnesium sulfate and evaporated to the dry state in a vacuum. The residue is chromatographed on silica gel (mobile solvent: dichloromethane/acetone=15:1).

Yield: 27.62 g (85% of theory)

Elementary analysis:

| Cld: | C 34.30 | H 3.03 | N 2.11 | F 48.54 |
|---|---|---|---|---|
| Fnd: | C 34.15 | H 3.19 | N 2.04 | F 48.37 | b) N-(1-Hydroxymethyl-2,3-dihydroxypropyl)-N-(1H,1H,2H,2H,4H,4H,5H,5H-3-oxaperfluorotridecyl)-amine 27 g (40.58 mmol) of the title compound of Example 9a is dissolved in 300 ml of tetrahydrofuran, and 26 ml of 10 M boranedimethyl sulfide (in tetrahydrofuran) is added. It is refluxed for 20 hours. It is cooled to 0° C., and 300 ml of methanol is added in drops, then it is evaporated to the dry state in a vacuum. The residue is taken up in a mixture that consists of 300 ml of ethanol/100 ml of 10% aqueous hydrochloric acid, and it is stirred for 6 hours at 60° C. It is evaporated to the dry state in a vacuum, the residue is taken up in 400 ml of 5% aqueous sodium hydroxide solution, and it is extracted 5 times with 250 ml of chloroform each. The organic phases are dried on magnesium sulfate, evaporated to the dry state in a vacuum, and the residue is chromatographed on silica gel (mobile solvent: dichloromethane/methanol=6:1).

Yield: 20.09 g (81% of theory) of a colorless solid

Elementary analysis:

| Cld: | C 31.44 | H 2.97 | N 2.29 | F 52.83 |
|---|---|---|---|---|
| Fnd: | C 31.26 | H 3.11 | N 2.18 | F 52.67 | c) 1,4,7-Tris(carboxylatomethyl)-10-{(3-aza-4-oxo-hexan-5-ylic)-acid-[N-1-hydroxymethyl-2,3-dihydroxypropyl)-N-(1H,1H,2H,2H,4H,4H,5H,5H-3-oxa-perfluorotridecyl]-amide}-1,4,7,10-tetraazacyclododecane, gadolinium complex 10 g (15.88 mmol) of the gadolinium complex of 10-[1-(carboxymethylcarboamoyl)-ethyl]-1,4,7,10-tetraazacyclododecane-1,4,7-triacetic acid and 1.35 g (31.76 mmol) of lithium chloride are dissolved at 60° C. in 100 ml of dimethyl sulfoxide. It is cooled to 15° C., and 9.71 (15.88 mmol) of the title compound of Example 9b is added. It is stirred for 10 minutes, and then 7.42 g (30 mmol) of 2-ethoxy-1-ethoxycarbonyl-1,3-dihydroquinoline is added. It is stirred for 12 hours at room temperature. The solution is poured into a mixture that consists of 200 ml of acetone/ 1300 ml of diethyl ether, and it is stirred for 2 hours at room temperature. The deposited precipitate is filtered off, dissolved in a mixture that consists of a little ethanol/water and chromatographed on silica gel RP-18 (mobile solvent: gradient that consists of tetrahydrofuran/acetonitrile/water).

Yield: 13.40 g (69% of theory) of a colorless, amorphous powder

Water content: 9.1%

Elementary analysis (relative to anhydrous substance):

| Cld: | C 34.37 | H 3.79 | N 6.87 | F 24.41 | Gd 12.86 |
|---|---|---|---|---|---|
| Fnd: | C 34.18 | H 3.95 | N 6.71 | F 24.25 | Gd 12.70 |

EXAMPLE 10 a) Perfluorooctylsulfonic acid-N-[(2-benzyloxycarbonylamino)-ethyl]-amide 40 g (173.4 mmol) of 1-benzyloxycarbonylamino-2-aminoethane, hydrochloride, 87.1 g (173.4 mmol) of perfluorooctylsulfofluoride and 35.42 g (350 mmol) of triethylamine are heated for 10 hours to 80° C. It is cooled to room temperature and added directly to a silica gel column for chromatographic purification (mobile solvent: dichloromethane/acetone=20:1).

Yield: 42.22 g (36% of theory) of a colorless solid

Elementary analysis:

| Cld: | C 31.97 | H 1.94 | N 4.14 | F 47.75 | S 4.74 |
|---|---|---|---|---|---|
| Fnd: | C 31.83 | H 2.11 | N 4.03 | F 47.63 | S 4.63 | b) Perfluorooctylsulfonic acid-N-[(2-amino)-ethyl]-amide 30 g (44.36 mmol) of the title compound of Example 10a is dissolved in 300 ml of methanol, and 5 g of palladium catalyst (10% Pd/c) is added, and it is hydrogenated overnight at room temperature. Catalyst is filtered off, and the filtrate is evaporated to the dry state in a vacuum.

Yield: 24.05 g (quantitative) of a colorless solid
Elementary analysis:

| Cld: | C 22.15 | H 1.30 | N 5.17 | F 59.57 |
|---|---|---|---|---|
| Fnd: | C 22.04 | H 1.41 | N 5.05 | F 59.62 | c) 1,4,7-Tris(carboxylatomethyl)-10-{(3-aza-4-oxo-hexan-5-ylic)-acid-N-[(2-perfluorooctylsulfonylamino)-ethyl]-amide}-1,4,7,10-tetraazacyclododecane, gadolinium complex 10 g (15.88 mmol) of the gadolinium complex of 10-[1-(carboxymethylcarboamoyl)-ethyl]-1,4,7,10-tetraazacyclododecane-1,4,7-triacetic acid and 1.35 g (31.76 mmol) of lithium chloride and 3.66 g (31.76 mmol) of N-hydroxysuccinimide are dissolved at 60° C. in 100 ml of dimethyl sulfoxide. It is cooled to 15° C., and 3.51 (17 mmol) of N,N'-dicyclohexylcarbodiimide is added and stirred for 5 hours at 15° C. To separate the urea, the solution is filtered. 8.61 g (15.88 mmol) of the title compound of Example 10b and 2.02 g (20 mmol) of triethylamine are added to the filtrate, and it is stirred for 12 hours at room temperature. The solution is poured into 1500 ml of diethyl ether/100 ml of acetone, and it is stirred for 30 minutes. The precipitated solid is filtered off and chromatographed on silica gel RP-18 (mobile solvent: gradient that consists of tetrahydrofuran/acetonitrile/water).

Yield: 15.76 g (86% of theory) of a colorless, amorphous powder
Water content: 6.5%
Elementary analysis (relative to anhydrous substance):

| Cld: | C 30.19 | H 3.06 | N 8.50 | F 27.99 | Gd 13.63 | S 2.78 |
|---|---|---|---|---|---|---|
| Fnd: | C 30.03 | H 3.18 | N 8.41 | F 27.81 | Gd 13.50 | S 2.61 |

EXAMPLE 11 a) 2H,2H,4H,4H,5H,5H-3-Oxa-perfluorotridecanoic acid-N-(2-benzyloxy-carboxylamino-ethyl]-amide 8.90 g (70 mmol) of oxalyl chloride is added to 30 g (57.45 mmol) of 2H,2H,4H,4H,5H,5H-3-oxa-perfluorotridecanoic acid in 300 ml of dichloromethane, and it is stirred for 12 hours at room temperature. It is evaporated to the dry state in a vacuum. The residue is dissolved in 100 ml of dichloromethane and added in drops at 0° C. to a solution of 13.84 g (60 mmol) of 1-benzyloxycarbonylamine-2-amino-ethane, hydrochloride and 12.14 g (120 mmol) of triethylamine, dissolved in 200 ml of dichloromethane. It is stirred for 3 hours at 0° C., then for 5 hours at room temperature. 300 ml of 5% aqueous hydrochloric acid is added, and it is thoroughly stirred for 15 minutes. The organic phase is separated, dried on magnesium sulfate and evaporated to the dry state in a vacuum. The residue is chromatographed on silica gel (mobile solvent: dichloromethane/acetone=20:1).

Yield: 33.30 g (83% of theory) of a colorless solid
Elementary analysis:

| Cld: | C 37.84 | H 2.74 | N 4.01 | F 46.25 |
|---|---|---|---|---|
| Fnd: | C 37.67 | H 2.89 | N 3.88 | F 46.11 | b) 2H,2H,4H,4H,5H,5H-3-Oxa-perfluorotridecanoic acid-N-[(2-amino)-ethyl]-amide 30 g (42.96 mmol) of the title compound of Example 11a is dissolved in 500 ml of methanol, and 5 g of palladium catalyst (10Pd/C) is added, and it is hydrogenated overnight at room temperature. It is filtered off into the catalyst, and the filtrate is evaporated to the dry state in a vacuum.

Yield: 24.24 g (quantitative) of a colorless solid
Elementary analysis:

| Cld: | C 29.80 | H 2.32 | N 4.96 | F 57.24 |
|---|---|---|---|---|
| Fnd: | C 29.67 | H 2.41 | N 4.88 | F 57.15 | c) 1,4,7-Tris-(carboxylatomethyl)-10-{(3-aza-4-oxo-hexan-5-ylic)-acid-N-[3-aza-6-oxa-4-oxo-($C_9$–$C_{16}$-heptadecafluoro)-hexadecyl]-amide}-1,4,7,10-tetraazacyclododecane-gadolinium complex 10 g (15.88 mmol) of the gadolinium complex of 10-[1-(carboxymethylcarboamoyl)-ethyl]-1,4,7,10-tetraazacyclododecane-1,4,7-triacetic acid and 1.35 g (31.76 mmol) of lithium chloride and 3.66 g (31.76 mmol) of N-hydroxysuccinimide are dissolved at 60° C. in 100 ml of dimethyl sulfoxide. It is cooled to 15° C., and 3.51 (17 mmol) of N,N'-dicyclohexylcarbodiimide is added, and it is stirred for 5 hours at 15° C. To separate the urea, the solution is filtered. 8.96 g (15.88 mmol) of the title compound of Example 11b and 2.02 g (20 mmol) of triethylamine are added to the filtrate, and it is stirred for 12 hours at room temperature. The solution is poured into 1500 ml of diethyl ether/100 ml of acetone, and it is stirred for 30 minutes. The precipitated solid is filtered off and chromatographed on silica gel RP-18 (mobile solvent: gradient that consists of tetrahydrofuran/acetonitrile/water).

Yield: 15.31 g (82% of theory) of a colorless, amorphous powder
Water content: 6.3%
Elementary analysis (relative to anhydrous substance):

| Cld: | C 33.71 | H 3.51 | N 8.34 | F 27.46 | Gd 13.37 |
|---|---|---|---|---|---|
| Fnd: | C 33.61 | H 3.63 | N 8.17 | F 27.31 | Gd 13.20 |

EXAMPLE 12 a) 2H,2H,4H,4H,5H,5H-3-Oxa-perfluoroundecanoic acid-N-[(2-hydroxy)-ethyl]-amide 8.90 g (70 mmol) of oxalyl chloride is added to 24.25 g (57.45 mmol) of 2H,2H,4H,4H,5H,5H-3-oxa-perfluorotridecanoic acid in 300 ml of dichloromethane, and it is stirred for 12 hours at room temperature. It is evaporated to the dry state in a vacuum. The residue is dissolved in 100 ml of dichloromethane and added in drops at 0° C. to a solution that consists of 3.66 g (60 mmol) of ethanolamine and 6.07 g (60 mmol) of triethylamine, dissolved in 200 ml of dichloromethane. It is stirred for 3 hours at 0° C., then for 6 hours at room temperature. 300 ml of 5% aqueous hydrochloric acid is added, and it is thoroughly stirred for 15 minutes. The organic phase is separated, dried on magnesium sulfate and evaporated to the dry state in a vacuum. The residue is chromatographed on silica gel (mobile solvent: dichloromethane/acetone=20:1).

Yield: 24.86 g (93% of theory) of a colorless solid
Elementary analysis:

| Cld: | C 30.98 | H 2.60 | N 3.01 | F 53.09 |
|---|---|---|---|---|
| Fnd: | C 30.71 | H 2.81 | N 2.87 | F 52.82 | b) N-(2-Hydroxyethyl)-N-1H,1H,2H,2H,4H,4H,5H,5H-3-oxa-perfluoroundecyl)-amine 24 g (51.59 mmol) of the title compound of Example 12a is dissolved in 300 ml of tetrahydrofuran, and 31 ml of 10 M boranedimethyl sulfide (in tetrahydrofuran) is added. It is refluxed for 12 hours. It is cooled to 0° C. and 200 ml of methanol is added in drops, then it is evaporated to the dry state in a vacuum. The residue is taken up in a mixture that consists of 300 ml of ethanol/50 ml of 10% aqueous hydrochloric acid, and it is stirred for 8 hours at 40° C. It is evaporated to the dry state in a vacuum, the residue is taken up in 300 ml of 5% aqueous sodium hydroxide solution, and it is extracted 3 times with 300 ml of dichloromethane each. The organic phases are dried on magnesium sulfate, evaporated to the dry state in a vacuum, and the residue is chromatographed on silica gel (mobile solvent: dichloromethane/2-propano=20:1).

Yield: 20.95 g (90% of theory) of a colorless solid
Elementary analysis:

| Cld: | C 31.94 | H 3.13 | N 3.10 | F 54.73 |
|---|---|---|---|---|
| Fnd: | C 31.71 | H 3.31 | N 3.01 | F 54.58 | c) 1,4,7-Tris-(carboxylatomethyl)-10-{(3-aza-4-oxo-hexan-5-ylic)-acid-N-[(2-hydroxy)-ethyl-N-(1H,1H,2H,2H,4H,4H,5H,5H-3-oxa)-perfluoroundecyl]-amide}-1,4,7,10-tetraazacyclododecane-gadolinium complex 10 g (15.88 mmol) of the gadolinium complex of 10-[1-(carboxymethylcarboamoyl)-ethyl]-1,4,7,10-tetraazacyclododecane-1,4,7-triacetic acid and 1.35 g (31.76 mmol) of lithium chloride are dissolved at 60° C. in 100 ml of dimethyl sulfoxide. It is cooled to 15° C., and 8.98 (15.88 mmol) of the title compound of Example 12b is added. It is stirred for 10 minutes, and then 7.42 g (30 mmol) of 2-ethoxy-1-ethoxycarbonyl-1,2-dihydroquinoline is added. It is stirred for 12 hours at room temperature. The solution is poured into a mixture that consists of 200 ml of acetone/1300 ml of diethyl ether, and it is stirred for 2 hours at room temperature. The deposited precipitate is filtered off, dissolved in a mixture that consists of a little ethanol/water and chromatographed on silica gel RP-18 (mobile solvent: gradient that consists of tetrahydrofuran/acetonitrile/water)

Yield: 14.01 g (83% of theory) of a colorless, amorphous powder
Elementary analysis:

| Cld: | C 35.03 | H 3.98 | N 7.91 | F 23.24 | Gd 14.79 |
|---|---|---|---|---|---|
| Fnd: | C 34.85 | H 4.19 | N 7.75 | F 23.05 | Gd 14.58 |

EXAMPLE 13 a) 2H,2H,4H,4H,5H,5H-3-Oxa-perfluoroundecanoic acid-N-(3,6,9,12-tetraoxa-tridecyl)-amide 8.90 g (70 mmol) of oxalyl chloride is added to 24.25 g (57.45 mmol) of 2H,2H,4H,4H,5H,5H-3-oxa-perfluoroundecanoic acid in 300 ml of dichloromethane, and it is stirred for 12 hours at room temperature. It is evaporated to the dry state in a vacuum. The residue is dissolved in 100 ml of dichloromethane and added in drops at 0° C. to a solution that consists of 12.44 g (60 mmol) of 3,6,9,12-tetraoxa-tridecylamine and 6.07 g (60 mmol) of triethylamine, dissolved in 200 ml of dichloromethane. It is stirred for 3 hours at 0° C., then for 6 hours at room temperature. 300 ml of 5% aqueous hydrochloric acid is added, and it is thoroughly stirred for 15 minutes. The organic phase is separated, dried on magnesium sulfate and evaporated to the dry state in a vacuum. The residue is chromatographed on silica gel (mobile solvent: dichloromethane/acetone=15:1).

Yield: 31.61 g (90% of theory) of a colorless solid
Elementary analysis:

| Cld: | C 37.33 | H 4.29 | N 2.29 | F 40.40 |
|---|---|---|---|---|
| Fnd: | C 37.15 | H 4.41 | N 2.12 | F 40.18 | b) N-(3,6,9,12-Tetraoxatridecyl)-N-(1H,1H,2H,2H,4H,4H,5H,5H-3-oxa-perfluoroundecyl)-amine 31 g (50.7 mmol) of the title compound of Example 13a is dissolved in 300 ml of tetrahydrofuran, and 32 ml of 10 M boranedimethyl sulfide (in tetrahydrofuran) is added. It is refluxed for 16 hours. It is cooled to 0° C., and 200 ml of methanol is added in drops, and then it is evaporated to the dry state in a vacuum. The residue is taken up in a mixture that consists of 300 ml of ethanol/50 ml of 10% aqueous hydrochloric acid, and it is stirred for 8 hours at 40° C. It is evaporated to the dry state in a vacuum, the residue is taken up in 300 ml of 5% aqueous sodium hydroxide solution, and it is extracted 3 times with 300 ml of dichloromethane each. The organic phases are dried on magnesium sulfate, evaporated to the dry state in a vacuum, and the residue is chromatographed on silica gel (mobile solvent: dichloromethane/2-propanol=20:1).

Yield: 28.17 g (93% of theory) of a colorless solid
Elementary analysis (relative to anhydrous substance):

| Cld: | C 38.20 | H 4.72 | N 2.34 | F 41.34 |
|---|---|---|---|---|
| Fnd: | C 38.05 | H 4.83 | N 2.40 | F 41.50 | c) 1,4,7-Tris-(carboxylatomethyl)-10-{(3-aza-4-oxo-hexan-5-ylic)-acid-N-[(3,6,9,12-tetraoxa)-tridecyl-N-(1H,1H,2H,2H,4H,4H,5H,5H-3-oxa)-perfluoroundecyl]-amide}-1,4,7,10-tetraazacyclododecane-gadolinium complex 10 g (15.88 mmol) of the gadolinium complex of 10-[1-(carboxymethylcarboamoyl)-ethyl]-1,4,7,10-tetraazacyclododecane-1,4,7-triacetic acid and 1.35 g (31.76 mmol) of lithium chloride are dissolved at 60° C. in 100 ml of dimethyl sulfoxide. It is cooled to 15° C., and 9.49 (15.88 mmol) of the title compound of Example 13b is added. It is stirred for 10 minutes, and then 7.42 g (30 mmol) of 2-ethoxy-1-ethoxycarbonyl-1,2-dihydroquinoline is added. It is stirred for 12 hours at room temperature. The solution is poured into a mixture that consists of 200 ml of acetone/1300 ml of diethyl ether, and it is stirred for 2 hours at room temperature. The deposited precipitate is filtered off, dissolved in a mixture that consists of a little ethanol/water and chromatographed on silica gel RP-18 (mobile solvent: gradient that consists of tetrahydrofuran/acetonitrile/water).

Yield: 16.13 g (84% of theory)
Elementary analysis:

| Cld: | C 37.75 | H 4.67 | N 6.95 | F 20.43 | Gd 13.01 |
|---|---|---|---|---|---|
| Fnd: | C 37.91 | H 4.81 | N 6.83 | P 20.60 | Gd 13.15 |

EXAMPLE 14 a) 2-N-(1H,1H,2H,2H,4H,4H,5H,5H-3-Oxa-perfluorotridecyl)-amino-acetic acid-t-butylester 6.523 g (40 mmol) of bromoacetic acid-t-butylester is added in drops to 32.0 g (58.65 mmol) of the title compound of Example 5b and 24.89 g (180 mmol) of potassium carbonate in 300 ml of acetonitrile at 50° C., and it is stirred for 3 hours at this temperature. 300 ml of dichloromethane is added, precipitated salts are filtered out, and the filtrate is evaporated to the dry state in a vacuum. The residue is chromatographed on silica gel (mobile solvent: dichloromethane/2-propanol=20:1).

Yield: 28.11 g (57% of theory) of a colorless solid
Elementary analysis:

| | | | | |
|---|---|---|---|---|
| Cld: | C 34.80 | H 3.24 | N 2.25 | F 51.98 |
| Fnd: | C 34.98 | H 3.31 | N 2.20 | F 52.16 | b) 1,4,7-Tris-(carboxylatomethyl)-10-{(3-aza-4-oxo-hexan-5-ylic)-acid-N-[(t-butyloxycarbonylmethyl)-N-(1H,1H,2H,2H,4H,4H,5H,5H-3-oxa)-perfluorotridecyl]-amide}-1,4,7,10-tetraazacyclododecane-gadolinium complex 10 g (15.88 mmol) of the gadolinium complex of 10-[1-(carboxymethylcarboamoyl)-ethyl]-1,4,7,10-tetraazacyclododecane-1,4,7-triacetic acid and 1.35 g (31.76 mmol) of lithium chloride are dissolved at 60° C. in 100 ml of dimethyl sulfoxide. It is cooled to 15° C., and 9.87 (15.88 mmol) of the title compound of Example 14a is added. It is stirred for 10 minutes, and then 7.42 g (30 mmol) of 2-ethoxy-1-ethoxycarbonyl-1,2-dihydroquinoline is added. It is stirred for 12 hours at room temperature. The solution is poured into a mixture that consists of 200 ml of acetone/1300 ml of diethyl ether, and it is stirred for 2 hours at room temperature. The deposited precipitate is filtered off, dissolved in a mixture that consists of a little ethanol/water and chromatographed on silica gel RP-18 (mobile solvent: gradient that consists of tetrahydrofuran/acetonitrile/water).

Yield: 16.64 g (85% of theory)
Elementary analysis:

| | | | | | |
|---|---|---|---|---|---|
| Cld: | C 36.04 | H 3.92 | N 6.82 | F 26.19 | Gd 12.72 |
| Fnd: | C 35.92 | H 3.83 | N 6.91 | F 26.29 | Gd 12.84 | c) 1,4,7-Tris-(carboxylatomethyl)-10-{(3-aza-4-oxo-hexan-5-ylic)-acid-N-[(carboxymethyl)-N-(1H,1H,2H,2H,4H,4H,5H,5H-3-oxa)-perfluorotridecyl]-amide}-1,4,7,10-tetraazacyclododecane-gadolinium complex 10 g (8.11 mmol) of the title compound of Example 14b is dissolved in 50 ml of trifluoroacetic acid, and it is stirred for 5 hours at room temperature. It is evaporated to the dry state in a vacuum, and the residue is chromatographed on silica gel RP-18 (mobile solvent: gradient that consists of tetrahydrofuran/acetonitrile/water). After the product-containing fractions are concentrated by evaporation, the residue is dissolved in water and set at pH 7.2 with 5% aqueous sodium hydroxide solution. The solution is filtered, and the filtrate is freeze-dried.

Yield: 10.48 g (91% of theory)
Elementary analysis (relative to anhydrous substance):

| | | | | | | |
|---|---|---|---|---|---|---|
| Cld: | C 33.06 | H 3.28 | N 7.01 | F 26.94 | Gd 13.12 | Na 1.92 |
| Fnd: | C 33.19 | H 3.40 | N 7.20 | F 27.14 | Gd 13.25 | Na 2.00 |

EXAMPLE 15 a) 2H,2H,4H,4H,5H,5H-3-Oxa-perfluorotridecanoic acid-N-(2-hydroxyethyl)-amide 2.96 g (74 mmol) of sodium hydride (that consists of 60% sodium hydride in paraffin oil) in 300 ml of tetrahydrofuran is added to 32 g (56.61 mmol) of the title compound of Example 4a, and it is stirred for 3 hours at room temperature under nitrogen. 7.67 g (74 mmol) of bromoacetic acid-t-butyl ester, dissolved in 20 ml of tetrahydrofuran, is added in drops, and it is stirred for 5 hours at 50° C. 50 ml of methanol is added, and it is evaporated to the dry state in a vacuum. The residue is chromatographed on silica gel (mobile solvent: dichloromethane (/2-propanol=20:1).

Yield: 23.46 g (61% of theory)
Elementary analysis:

| | | | | |
|---|---|---|---|---|
| Cld: | C 35.36 | H 3.26 | N 2.06 | F 47.54 |
| Fnd: | C 35.52 | H 3.40 | N 2.17 | F 47.40 | b) N-(1H,1H,2H,2H,4H,4H,5H,5H-3-Oxa-perfluorotridecyl)-N-[4-t-butyloxycarbonyl-3-oxa)-butyl]-amine 35.0 g (51.52 mmol) of the title compound of Example 15a is dissolved in 300 ml of tetrahydrofuran, and 31 ml of 10 M boranedimethyl sulfide (in tetrahydrofuran) is added. It is refluxed for 16 hours. It is cooled to 0° C., and 200 ml of methanol is added in drops, then it is evaporated to the dry state in a vacuum. The residue is taken up in a mixture that consists of 300 ml of ethanol/50 ml of 10% aqueous hydrochloric acid, and it is stirred for 8 hours at 40° C. It is evaporated to the dry state in a vacuum, the residue is taken up in 300 ml of 5% aqueous sodium hydroxide solution and extracted 3 times with 300 ml of dichloromethane each. The organic phases are dried on magnesium sulfate, evaporated to the dry state in a vacuum, and the residue is chromatographed on silica gel (mobile solvent: dichloromethane/2-propanol=20:1).

Yield: 31.88 g (93% of theory)
Elementary analysis:

| | | | | |
|---|---|---|---|---|
| Cld: | C 36.10 | H 3.64 | N 2.11 | F 48.54 |
| Fnd: | C 35.90 | H 3.75 | N 2.20 | F 48.71 | c) 1,4,7-Tris-(carboxylatomethyl)-10-{(3-aza-4-oxo-hexan-5-ylic)-acid-N-[(4-t-butyloxycarbonyl-3-oxa)-butyl)-N-(1H,1H,2H,2H,4H,4H,5H,5H-3-oxa)-perfluorotridecyl]-amide)}-1,4,7,10-tetraazacyclododecane, gadolinium complex 10 g (15.88 mmol) of the gadolinium complex of 10-[1-(carboxymethylcarboamoyl)-ethyl]-1,4,7,10-tetraazacyclododecane-1,4,7-triacetic acid and 1.35 g (31.76 mmol) of lithium chloride are dissolved at 60° C. in 100 ml of dimethyl sulfoxide. It is cooled to 15° C., and 10.57 (15.88 mmol) of the title compound of Example 15b is added. It is stirred for 10 minutes, and then 7.42 g (30 mmol) of 2-ethoxy-1-ethoxycarbonyl-1,2-dihydroquinoline is added. It is stirred for 12 hours at room temperature. The solution is poured into a mixture that consists of 200 ml of a acetone/1300 ml of diethyl ether, and it is stirred for 2 hours at room temperature. The deposited precipitate is filtered off, dissolved in a mixture that consists of a little ethanol/water and chromatographed in silica gel RP-18 (mobile solvent: gradient that consists of tetrahydrofuran/acetonitrile/water).

Yield: 16.63 g (82% of theory)
Elementary analysis:

| | | | | | |
|---|---|---|---|---|---|
| Cld: | C 36.68 | H 4.10 | N 6.58 | F 25.29 | Gd 12.31 |
| Fnd: | C 36.81 | H 4.20 | N 6.41 | F 25.40 | Gd 12.19 | d) 1,4,7-Tris-(carboxylatomethyl)-10-{(3-aza-4-oxo-hexan-5-ylic)-acid-[N-(4-carboxy-3-oxa)-butyl)-N-(1H,1H,2H,2H,4H,4H,5H,5H-3-oxa)-perfluorotridecyl]-amide}-1,4,7,10-tetraazacyclododecane, gadolinium complex 12 g (9.40 mmol) of the title compound of Example 15c is dissolved in 50 ml of trifluoroacetic acid, and it is stirred for 5 hours at room temperature. It is evaporated to the dry state in a vacuum, and the residue is chromatographed on silica gel RP-18 (mobile solvent: gradient that consists of tetrahydrofuran/acetonitrile/water). After the product-containing fractions are concentrated by evaporation, the residue is dissolved in water and set at pH 7.2 with 5% aqueous sodium hydroxide solution. The solution is filtered, and the filtrate is freeze-dried.

Yield: 11.41 g (92% of theory)

Water content: 5.8%

Elementary analysis (relative to anhydrous substance):

| Cld: | C 33.82 | H 3.49 | N 6.76 | F 25.98 | Gd 12.65 | Na 1.85 |
|---|---|---|---|---|---|---|
| Fnd: | C 33.95 | H 3.60 | N 6.88 | F 26.15 | Gd 12.49 | Na 1.93 |

EXAMPLE 16 a) 2H,2H,4H,4H,5H,5H-3-Oxa-perfluorotridecanoic acid-N-(2H,2H,4H,4H,5H,5H-3-oxa-perfluorotridecyl)-amide 8.90 g (70 mmol) of oxalyl chloride is added to 30 g (57.45 mmol) of 2H,2H,4H,4H,5H,5H-3-oxa-perfluorotridecanoic acid in 300 ml of dichloromethane, and it is stirred for 12 hours at room temperature. It is evaporated to the dry state in a vacuum. The residue is dissolved in 100 ml of dichloromethane, and added in drops at 0° C. to a solution that consists of 32.62 g (60 mmol) of the title compound of Example 5b and 6.07 g (60 mmol) of triethylamine, dissolved in 200 ml of dichloromethane. It is stirred for 3 hours at 0° C., then for 6 hours at room temperature. 300 ml of 5% aqueous hydrochloric acid is added, and it is thoroughly stirred for 15 minutes. The organic phase is separated, dried on magnesium sulfate and evaporated to the dry state in a vacuum. The residue is chromatographed on silica gel (mobile solvent: dichloromethane/acetone=15:1).

Yield: 52.87 g (91% of theory)

Elementary analysis:

| Cld: | C 28.50 | H 1.49 | N 1.38 | F 63.87 |
|---|---|---|---|---|
| Fnd: | C 28.65 | H 1.61 | N 1.50 | F 64.01 | b) N-Bis-(1H,1H,2H,2H,4H,4H,5H,5H-3-oxa)-perfluorotridecyl)-amine 52 g (51.42 mmol) of the title compound of Example 16a is dissolved in 500 ml of tetrahydrofuran, and 31 ml of 10 M boranedimethyl sulfide (in tetrahydrofuran) is added. It is refluxed for 16 hours. It is cooled to 0° C., and 200 ml of methanol is added in drops, then it is evaporated to the dry state in a vacuum. The residue is taken up in a mixture that consists of 400 ml of ethanol/70 ml of 10aqueous hydrochloric acid, and it is stirred for 8 hours at 40° C. It is evaporated to the dry state in a vacuum, the residue is taken up in 400 ml of 5% aqueous sodium hydroxide solution, and it is extracted 3 times with 400 ml of dichloromethane each. The organic phases are dried on magnesium sulfate, evaporated to the dry state in a vacuum, and the residue is chromatographed on silica gel (mobile solvent: dichloromethane/2-propanol=20:1).

Yield: 47.18 g (92% of theory) of a colorless solid

Elementary analysis:

| Cld: | C 28.90 | H 1.72 | N 1.40 | F 64.77 |
|---|---|---|---|---|
| Fnd: | C 30.03 | H 1.81 | N 1.55 | F 65.00 | c) 1,4,7-Tris(carboxylatomethyl)-10-[(3-aza-4-oxo-hexan-5-ylic)-acid-N-bis-(1H,1H,2H,2H,4H,4H,5H,5H-3-oxaperfluorotridecyl)-amide]-1,4,7,10-tetraazacyclododecane, gadolinium complex 10 g (15.88 mmol) of the gadolinium complex of 10-[1-(carboxymethylcarboamoyl)-ethyl]-1,4,7,10-tetraazacyclododecane-1,4,7-triacetic acid and 1.35 g (31.76 mmol) of lithium chloride are dissolved at 60° C. in 100 ml of dimethyl sulfoxide. It is cooled to 15° C., and 15.84 (15.88 mmol) of the title compound of Example 16b is added. It is stirred for 10 minutes, and then 7.42 g (30 mmol) of 2-ethoxy-1-ethoxycarbonyl-1,2-dihydroquinoline is added. It is stirred for 12 hours at room temperature. The solution is poured into a mixture that consists of 200 ml of acetone/1300 ml of diethyl ether, and it is stirred for 2 hours at room temperature. The deposited precipitate is filtered off, dissolved in a mixture that consists of a little ethanol/water and chromatographed on silica gel RP-18 (mobile solvent: gradient that consists of tetrahydrofuran/acetonitrile/water).

Yield: 20.95 g (82% of theory)

Elementary analysis:

| Cld: | C 22.10 | H 2.82 | N 5.22 | F 40.14 | Gd 9.77 |
|---|---|---|---|---|---|
| Fnd: | C 29.87 | H 2.91 | N 5.09 | F 40.28 | Gd 9.98 |

EXAMPLE 17 a) 2H,2H,4H,4H,5H,5H-3-Oxa-perfluorotridecanoic acid-N-(5-hydroxy-3-oxa-pentyl)-amide 2.80 g (70 mmol) of sodium hydride (that consists of 60% sodium hydride in paraffin oil) in 300 ml of tetrahydrofuran is added to 32 g (52.52 mmol) of the title compound of Example 3a, and it is stirred for 3 hours at room temperature under nitrogen. 9.68 g (70 mmol) of bromoacetic acid-t-butylester, dissolved in 20 ml of tetrahydrofuran, is added in drops, and it is stirred for 5 hours at 50° C. 50 ml of methanol is added, and it is evaporated to the dry state in a vacuum. The residue is chromatographed on silica gel (mobile solvent: dichloromethane (/2-propanol=20:1).

Yield: 19.31 g (59% of theory)

Elementary analysis:

| Cld: | C 32.76 | H 2.91 | N 2.25 | F 51.82 |
|---|---|---|---|---|
| Fnd: | C 32.98 | H 2.99 | N 2.36 | F 51.98 | b) N-(3,6-Dioxa-heptyl)-N-(1H,1H,2H,2H,4H,4H,5H,5H-3-oxa-perfluorotridecyl)-amine 32 g (51.34 mmol) of the title compound of Example 17a is dissolved in 300 ml of tetrahydrofuran, and 31 ml of 10 M boranedimethyl sulfide (in tetrahydrofuran) is added. It is refluxed for 16 hours. It is cooled to 0° C., and 200 ml of methanol is added in drops, then it is evaporated to the dry state in a vacuum. The residue is taken up in a mixture of 300 ml of ethanol/50 ml of 10% aqueous hydrochloric acid, and it is stirred for 8 hours at 40° C. It is evaporated to the dry state in a vacuum, the residue is taken up in 300 ml of 5% aqueous sodium hydroxide solution, and it is extracted 3 times with 300 ml of dichloromethane each. The organic phases are dried on magnesium sulfate, evaporated to the dry state in a vacuum, and the residue is chromatographed on silica gel (mobile solvent: dichloromethane/2-propanol 20:1).

Yield: 28.47 g (91% of theory)
Elementary analysis:

| Cld: | C 33.51 | H 3.31 | N 2.30 | F 53.01 |
|---|---|---|---|---|
| Fnd: | C 33.63 | H 3.41 | N 2.21 | F 52.87 | c) 1,4,7-Tris(carboxylatomethyl)-10-[(3-aza-4-oxo-hexan-5-ylic)-acid-N-(3,6-dioxa)-heptyl-N-(1H,1H,2H,2H,4H,4H,5H,5H-3-oxa-perfluorotridecyl)-amide]-1,4,7,10-tetraazacyclododecane, gadolinium complex 10 g (15.88 mmol) of the gadolinium complex of 10-[1-(carboxymethylcarboamoyl)-ethyl]-1,4,7,10-tetraazacyclododecane-1,4,7-triacetic acid and 1.35 g (31.76 mmol) of lithium chloride are dissolved at 60° C. in 100 ml of dimethyl sulfoxide. It is cooled to 15° C., and 9.68 (15.88 mmol) of the title compound of Example 17b is added. It is stirred for 10 minutes and then 7.42 g (30 mmol) of 2-ethoxy-1-ethoxycarbonyl-1,2-dihydroquinoline is added. It is stirred for 12 hours at room temperature. The solution is poured into a mixture that consists of 200 ml of acetone/1300 ml of diethyl ether, and it is stirred for 2 hours at room temperature. The deposited precipitate is filtered off, dissolved in a mixture that consists of a little ethanol/water and chromatographed on silica gel RP-18 (mobile solvent: gradient that consists of tetrahydrofuran/acetonitrile/water).

Yield: 16.09 g (83% of theory)
Elementary analysis:

| Cld: | C 35.41 | H 3.96 | N 6.88 | F 26.45 | Gd 12.88 |
|---|---|---|---|---|---|
| Fnd: | C 35.57 | H 4.11 | N 6.72 | F 26.58 | Gd 12.97 |

EXAMPLE 18 a) 2H,2H,4H,4H,5H,5H-3-Oxa-perfluorotridecanoic acid-N-(hexyl)-amide 8.90 g (70 mmol) of oxalyl chloride is added to 30 g (57.45 mmol) of 2H,2H,4H,4H,5H,5H-3-oxa-perfluorotridecanoic acid in 300 ml of dichloromethane, and it is stirred for 12 hours at room temperature. It is evaporated to the dry state in a vacuum. The residue is dissolved in 100 ml of dichloromethane and added in drops at 0° C. to a solution of 6.07 g (60 mmol) of n-hexylamine and 6.07 g (60 mmol) of triethylamine, dissolved in 200 ml of dichloromethane. It is stirred for 3 hours at 0° C., then for 6 hours at room temperature. 300 ml of 5% aqueous hydrochloric acid is added, and it is thoroughly stirred for 15 minutes. The organic phase is separated, dried on magnesium sulfate, and evaporated to the dry state in a vacuum. The residue is chromatographed on silica gel (mobile solvent: dichloromethane/acetone=20:1).

Yield: 30.95 g (89% of theory)
Elementary analysis:

| Cld: | C 35.72 | H 3.33 | N 2.31 | F 53.35 |
|---|---|---|---|---|
| Fnd: | C 35.60 | H 3.45 | N 2.43 | F 53.63 | b) N-(Hexyl)-N-(1H,1H,2H,2H,4H,4H,5H,5H-3-oxa-perfluorotridecyl)-amine 31 g (51.21 mmol) of the title compound of Example 18a is dissolved in 300 ml of tetrahydrofuran, and 31 ml of 10 M boranedimethyl sulfide (in tetrahydrofuran) is added. It is refluxed for 16 hours. It is cooled to 0° C., and 200 ml of methanol is added in drops, then it is evaporated to the dry state in a vacuum. The residue is taken up in a mixture of 300 ml of ethanol/50 ml of 10% aqueous hydrochloric acid, and it is stirred for 8 hours at 40° C. It is evaporated to the dry state in a vacuum, and the residue is taken up in 300 ml of 5% aqueous sodium hydroxide solution and extracted 3 times with 300 ml of dichloromethane each. The organic phases are dried on magnesium sulfate, evaporated to the dry state in a vacuum, and the residue is chromatographed on silica gel (mobile solvent: dichloromethane/2-propanol= 20:1).

Yield: 28.16 g (93% of theory)
Elementary analysis:

| Cld: | C 36.56 | H 3.75 | N 2.37 | F 54.62 |
|---|---|---|---|---|
| Fnd: | C 36.40 | H 3.82 | N 2.27 | F 54.81 | c) 1,4,7-Tris(carboxylatomethyl)-10-{(3-aza-4-oxo-hexan-5-ylic)-acid-[N-(hexyl)-N-(1H,1H,2H,2H,4H,4H,5H,5H-3-oxa-perfluorotridecyl]-amide}-1,4,7,10-tetraazacyclododecane, gadolinium complex 10 g (15.88 mmol) of the gadolinium complex of 10-[1-(carboxymethylcarboamoyl)-ethyl]-1,4,7,10-tetraazacyclododecane-1,4,7-triacetic acid and 1.35 g (31.76 mmol) of lithium chloride are dissolved at 60° C. in 100 ml of dimethyl sulfoxide. It is cooled to 15° C., and 10.98 (15.88 mmol) of the title compound of Example 18b is added. It is stirred for 10 minutes, and then 7.42 g (30 mmol) of 2-ethoxy-1-ethoxycarbonyl-1,2-dihydroquinoline is added. It is stirred for 12 hours at room temperature. The solution is poured into a mixture that consists of 200 ml of acetone/1300 ml of diethyl ether, and it is stirred for 2 hours at room temperature. The deposited precipitate is filtered, dissolved in a mixture that consists of a little ethanol/water and chromatographed on silica gel RP-18 (mobile solvent: gradient that consists of tetrahydrofuran/acetonitrile/water)

Yield: 16.29 g (84% of theory)
Elementary analysis:

| Cld: | C 36.94 | H 4.19 | N 6.99 | F 26.85 | Gd 13.07 |
|---|---|---|---|---|---|
| Fnd: | C 37.18 | H 4.31 | N 7.18 | F 26.67 | Gd 13.19 |

EXAMPLE 19 a) 2H,2H,4H,4H,5H,5H-3-Oxa-perfluorotridecanoic acid-N-[(10-t-butyloxycarbonyl)-decyl]-amide 8.90 g (70 mmol) of oxalyl chloride is added to 30 g (57.45 mmol) of 2H,2H,4H,4H,5H,5H-3-oxa-perfluorotridecanoic acid in 300 ml of dichloromethane, and it is stirred for 12 hours at room temperature. It is evaporated to the dry state in a vacuum. The residue is dissolved in 100 ml of dichloromethane and added in drops at 0° C. to a solution of 15.45 g (60 mmol) of 11-amino-undecanoic acid-t-butylester and 6.07 g (60 mmol) of triethylamine, dissolved in 200 ml of dichloromethane. It is stirred for 3 hours at 0° C., then for 6 hours at room temperature. 300 ml of 5% aqueous hydrochloric acid is added, and it is thoroughly stirred for 15 minutes. The organic phase is separated, dried on magnesium sulfate and evaporated to the dry state in a vacuum. The residue is chromatographed on silica gel (mobile solvent: dichloromethane/acetone=20:1).

Yield: 42.04 g (92% of theory)
Elementary analysis:

| Cld: | C 42.58 | H 4.76 | N 1.84 | F 42.41 |
|---|---|---|---|---|
| Fnd: | C 42.74 | H 4.90 | N 1.73 | F 42.61 | b) N-(10-t-Butyloxycarbonyl-decyl)-N-(1H,1H,2H,2H,4H,4H,5H,5H-3-oxa-perfluorotridecyl)-amine 39 g (51.21 mmol) of the title compound of Example 19a is dissolved in 300 ml of tetrahydrofuran, and 31 ml of 10 M boranedimethyl sulfide (in tetrahydrofuran) is added. It is refluxed for 16 hours. It is cooled to 0° C., and 200 ml of methanol is added in drops, then it is evaporated to the dry state in a vacuum. The residue is taken up in a mixture of 400 ml of ethanol/70 ml of 10% aqueous hydrochloric acid, and it is stirred for 8 hours at 40° C. It is evaporated to the dry state in a vacuum, the residue is taken up in 350 ml of 5% aqueous sodium hydroxide solution, and it is extracted 3 times with 400 ml of dichloromethane each. The organic phases are dried on magnesium sulfate, evaporated to the dry state in a vacuum, and the residue is chromatographed on silica gel (mobile solvent: dichloromethane/2-propanol=20:1).

Yield: 34.84 g (91% of theory)
Elementary analysis:

| Cld: | C 43.38 | H 5.12 | N 1.87 | F 43.20 |
|---|---|---|---|---|
| Fnd: | C 43.22 | H 5.23 | N 1.96 | F 43.33 | c) 1,4,7-Tris(carboxylatomethyl)-10-{(3-aza-4-oxo-hexan-5-ylic)-acid-[N-(10-t-butyloxycarbonyl)-decyl-N-(1H,1H,2H,2H,4H,4H,5H,5H-3-oxa-perfluorotridecyl]-amide}-1,4,7,10-tetraazacyclododecane, gadolinium complex 10 g (15.88 mmol) of the gadolinium complex of 10-[1-(carboxymethylcarboamoyl)-ethyl]-1,4,7,10-tetraazacyclododecane-1,4,7-triacetic acid and 1.35 g (31.76 mmol) of lithium chloride are dissolved at 60° C. in 100 ml of dimethyl sulfoxide. It is cooled to 15° C., and 11.87 (15.88 mmol) of the title compound of Example 19b is added. It is stirred for 10 minutes, and then 7.42 g (30 mmol) of 2-ethoxy-1-ethoxycarbonyl-1,2-dihydroquinoline is added. It is stirred for 12 hours at room temperature. The solution is poured into a mixture that consists of 200 ml of acetone/1300 ml of diethyl ether, and it is stirred for 2 hours at room temperature. The deposited precipitate is filtered off, dissolved in a mixture that consists of a little ethanol/water and chromatographed on silica gel RP-18 (mobile solvent: gradient that consists of tetrahydrofuran/acetonitrile/water).

Yield: 17.92 g (83% of theory)
Elementary analysis:

| Cld: | C 40.65 | H 4.89 | N 6.18 | F 23.76 | Gd 11.57 |
|---|---|---|---|---|---|
| Fnd: | C 40.81 | H 4.99 | N 6.32 | F 23.94 | Gd 11.73 | d) 1,4,7-Tris-(carboxylatomethyl)-10-{(3-aza-4-oxo-hexan-5-ylic)-acid-[N-(10-carboxy)-decyl-N-(1H,1H,2H,2H,4H,4H,5H,5H-3-oxa-perfluorotridecyl]-amide}-1,4,7,10-tetraazacyclododecane, gadolinium complex, sodium salt 12 g (8.83 mmol) of the title compound of Example 19c is dissolved in 50 ml of trifluoroacetic acid, and it is stirred for 5 hours at room temperature. It is evaporated to the dry state in a vacuum, and the residue is chromatographed on silica gel RP-18 (mobile solvent: gradient that consists of tetrahydrofuran/acetonitrile/water). After the product-containing fractions are concentrated by evaporation, the residue is dissolved in water and set at pH 7.2 with 5% aqueous sodium hydroxide solution. The solution is filtered, and the filtrate is freeze-dried.

Yield: 12.48 g (92% of theory)
Water content: 6.2%
Elementary analysis (relative to anhydrous substance):

| Cld: | C 38.07 | H 4.34 | N 6.34 | F 24.37 | Gd 11.87 | Na 1.73 |
|---|---|---|---|---|---|---|
| Fnd: | C 37.89 | H 4.44 | N 6.22 | F 24.51 | Gd 12.01 | Na 1.80 |

EXAMPLE 20 a) 15-Benzyl-3,6,9,12,15-pentaoxa-hexadecanoic acid-N-(1H,1H,2H,2H,4H,4H,5H,5H-3-oxa)-perfluorotridecyl)-amide 8.90 g (70 mmol) of oxalyl chloride is added to 19.67 g (57.45 mmol) of 15-benzyl-3,6,9,12,15-pentaoxahexadecanoic acid in 250 ml of dichloromethane, and it is stirred for 12 hours at room temperature. It is evaporated to the dry state in a vacuum. The residue is dissolved in 100 ml of dichloromethane and added in drops at 0° C. to a solution of 32.62 g (60 mmol) of 1H,1H,2H,2H,4H,4H,5H,5H-3-oxa-perfluoro-tridecylamine, hydrochloride and 6.07 g (60 mmol) of triethylamine, dissolved in 200 ml of dichloromethane. It is stirred for 3 hours at 0° C., then for 6 hours at room temperature. 300 ml of 5% aqueous hydrochloric acid is added, and it is thoroughly stirred for 15 minutes. The organic phase is separated, dried on magnesium sulfate and evaporated to the dry state in a vacuum. The residue is chromatographed on silica gel (mobile solvent: dichloromethane/acetone=20:1).

Yield: 44.91 g (94% of theory) of a colorless solid
Elementary analysis:

| Cld: | C 41.89 | H 4.12 | N 1.18 | F 38.84 |
|---|---|---|---|---|
| Fnd: | C 42.02 | H 4.25 | N 1.83 | F 39.07 | b) N-15-Benzyl-3,6,9,12,15-pentaoxa-hexadecyl)-N-(1H,1H,2H,2H,4H,4H,5H,5H-3-oxa)-perfluorotridecyl)-amine 43 g (51.72 mmol) of the title compound of Example 20a is dissolved in 400 ml of tetrahydrofuran, and 31 ml of 10 M boranedimethyl sulfide (in tetrahydrofuran) is added. It is refluxed for 16 hours. It is cooled to 0° C., and 200 ml of methanol is added in drops, then it is evaporated to the dry state in a vacuum. The residue is taken up in a mixture of 400 ml of ethanol/50 ml of 10% aqueous hydrochloric acid, and it is stirred for 8 hours at 40° C. It is evaporated to the dry state in a vacuum, the residue is taken up in 350 ml of 5% aqueous sodium hydroxide solution, and it is extracted 3 times with 400 ml of dichloromethane each. The organic phases are dried on magnesium sulfate, evaporated to the dry state in a vacuum, and the residue is chromatographed on silica gel (mobile solvent: dichloromethane/2-propanol=20:1).

Yield: 39.32 g (93% of theory)
Elementary analysis:

| Cld: | C 42.10 | H 4.12 | N 1.68 | F 38.84 |
|---|---|---|---|---|
| Fnd: | C 42.45 | H 4.23 | N 1.57 | F 38.99 | c) 1,4,7-Tris-(carboxylatomethyl)-10-{(3-aza-4-oxo-hexan-5-ylic)-acid-[N-(15-benzyl-3,6,9,12,15-pentaoxa)- hexadecyl-N-(1H,1H,2H,2H,4H,4H,5H,5H-3-oxa)-tridecyl]-amide}-1,4,7,10-tetraazacyclododecane, gadolinium complex 10 g (15.88 mmol) of the gadolinium complex of 10-[1-(carboxymethylcarboamoyl)-ethyl]-1,4,7,10-tetraaazacyclododecane-1,4,7-triacetic acid and 1.35 g (31.76 mmol) of lithium chloride are dissolved at 60° C. in 100 ml of dimethyl sulfoxide. It is cooled to 15° C., and 12.98 (15.88 mmol) of the title compound of Example 20b is added. It is stirred for 10 minutes, and then 7.42 g (30 mmol) of 2-ethoxy-1-ethoxycarbonyl-1,2-dihydroquinoline is added. It is stirred for 12 hours at room temperature. The solution is poured into a mixture that consists of 200 ml of acetone/1300 ml of diethyl ether, and it is stirred for 2 hours at room temperature. The deposited precipitate is filtered off, dissolved in a mixture that consists of a little ethanol/water and chromatographed on silica gel RP-18 (mobile solvent: gradient that consists of tetrahydrofuran/acetonitrile/water).

Yield: 18.84 g (83% of theory)

Elementary analysis:

| Cld: | C 40.34 | H 4.51 | N 5.88 | F 22.60 | Gd 11.00 |
|---|---|---|---|---|---|
| Fnd: | C 40.50 | H 4.62 | N 5.76 | F 22.73 | Gd 11.16 | d) 1,4,7-Tris-(carboxylatomethyl)-10-{(3-aza-4-oxo-hexan-5-ylic)-acid-[N-(14-hydroxy-3,6,9,12-tetraoxa)-tetradecyl-N-(1H,1H,2H,2H,4H,4H,5H,5H-3-oxa)-perfluorotridecyl]-amide}-1,4,7,10-tetraazacyclododecane, gadolinium complex 12 g (8.40 mmol) of the title compound of Example 20c is dissolved in 150 ml of methanol, and 1.0 g of palladium catalyst (10% Pd/C) is added, and it is hydrogenated overnight at room temperature. It is filtered off into the catalyst, and the filtrate is evaporated to the dry state in a vacuum.

Yield: 10.13 g (95% of theory)

Elementary analysis:

| Cld: | C 38.80 | H 4.61 | N 1.10 | F 25.45 | Gd 12.39 |
|---|---|---|---|---|---|
| Fnd: | C 38.87 | H 4.73 | N 1.20 | F 25.58 | Gd 12.50 |

EXAMPLE 21

In Vivo Comparison of the Compounds of Examples 4c and 5e with Dy-DTPA

Three 350 g male (Schering-SPF) rats are used as test animals. 0.33–0.37 ml (in each case 100 mmol/L) of the following contrast medium solution is administered intravenously to each animal: mixture of 1 part each of a perfluoroalkyl-containing compound and the dysprosium-complex of (Dy-DTPA). The administered dose is in each case 100 $\mu$mol of Gd or Dy/kg of body weight. Via a catheter in the common carotid artery, blood samples are taken at the following times: 1, 3, 5, 10, 15, 20, 30, 45, 60, 90, 120 minutes p.i. In the blood samples that are obtained, in each case the concentrations of gadolinium (Gd) and dysprosium (Dy) are measured in parallel using atomic emission spectrometry (ICP-AES). The proportion of the injected compounds (Gd-containing perfluoroalkyl-containing compound and Dy-containing comparison substance) that remains in the blood space can be compared in the same animal by the different labeling. The $\alpha$- and $\beta$-half life, the distribution volume and the total clearance can be calculated from the blood concentrations using special software (Topfit program). These data thus yield information on the compounds that remain in the intravascular space, the distribution conditions in the organism and the elimination. Results:

At all examination times, significantly higher blood concentrations of the perfluoroalkyl-containing compounds (substances from Example 4c or 5e) compared with the extracellular contrast media (Dy-DTPA) are obtained. In this respect, see FIGS. 1 and 2:

FIG. 1 shows the blood level (in % of the dose) of Gd (perfluoroalkyl-containing compound of Example 5e) and Dy (Dy-DTPA) after intravenous administration of 100 $\mu$mol/kg of body weight in rats in each case (n=3).

In Table 1, pharmacokinetics parameters (plasma) of the compound of Example 5e) and Dy-DTPA after intravenous administration of 100 $\mu$mol/kg of body weight in rats (n=3) are indicated in each case:

TABLE 1

|  |  | 5e | Dy-DTPA |
|---|---|---|---|
| $\alpha$-t½ | min | 3.77 ± 0.75 | 2.19 ± 0.59 |
| $\beta$-t½ | min | 102.29 ± 24.48 | 62.59 ± 37.47 |
| Vd ss | L/kg | 0.16 ± 0.03 | 0.29 ± 0.09 |
| Total Clearance | ml/min * kg | 1.22 ± 0.05 | 4.24 ± 1.52 |

Figure 2:
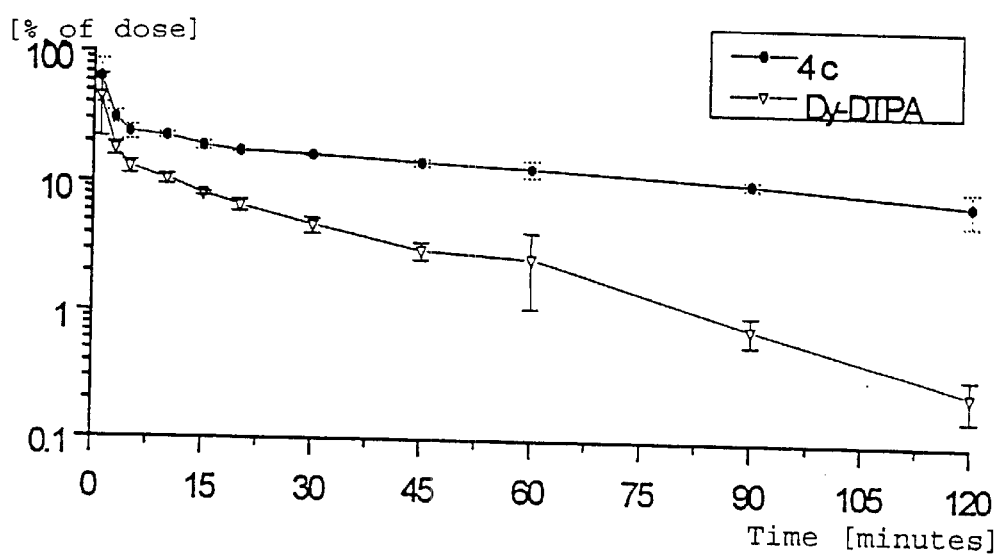
FIG. 2 shows the blood level (in % of the dose) of Gd (perfluoroalkyl-containing compound of Example 4c) and Dy (Dy-DTPA) after intravenous administration of 100 μmol/kg of body weight in rats in each case (n=3).

FIG. 2 shows the blood level (in % of the dose) of Gd (perfluoroalkyl-containing compound of Example 4c) and Dy (Dy-DTPA) after intravenous administration of 100 $\mu$mol/kg of body weight in rats in each case (n=3).

TABLE 2

|  |  | 4c | Dy-DTPA |
|---|---|---|---|
| $\alpha$-t½ | min | 1.01 ± 0.32 | 0.89 ± 0.32 |
| $\beta$-t½ | min | 79.68 ± 12.26 | 21.37 ± 2.18 |
| Vd ss | L/kg | 0.12 ± 0.00 | 0.15 ± 0.03 |
| Total Clearance | ml/min * kg | 1.14 ± 0.19 | 5.77 ± 1.08 |

In Table 2, the pharmacokinetics parameters (plasma) of compound 4c) and Dy-DTPA after intravenous administration of 100 $\mu$mol/kg of body weight in rats in each case (n=3) are indicated.

The considerably higher blood concentrations of the perfluoroalkyl-containing compounds (substances from Examples 4c or 5e) indicate a significantly smaller distribution volume compared to Dy-DTPA (see also Vd ss in Tables 1 and 2), i.e., these perfluoroalkyl-containing compounds are not dispersed as Dy-DTPA in the intravascular space (vessels) and in the extracellular space, but rather for the most part only in the intravascular space (especially at early times). Later on, the blood level of the perfluoroalkyl-containing compounds drops, but the elimination times or $\beta$-half lives are considerably shorter than in other blood-pool agents. The total blood clearance of the perfluoroalkyl-containing compounds is only slightly smaller compared to Dy-DTPA, which indicates a comparatively good renal elimination.

The perfluoroalkyl-containing compounds that are described in Example 21 show efficient elimination from the blood (via the kidneys), but a considerably smaller distribution volume than an extracellular contrast medium such as Dy-DTPA shows.

EXAMPLE 22

Lymph Node Concentration in Guinea Pigs

Different perfluoroalkyl-containing gadolinium complexes were studied 30 and 90 minutes after subcutaneous administration (10 $\mu$mol of total gadolinium/kg of body weight, hind paw s.c.) to stimulated guinea pigs (complete Freund adjuvant; in each case 0.1 ml of i.m. in the right and left upper and lower arm; 2 weeks before the administration of test substances) with respect to their lymph node concentration in three successive lymph node stations (popliteal, inguinal, iliac). In this connection, the results listed below (determination of the gadolinium concentration using ICP-AES) were obtained:

| | | Substance | | |
|---|---|---|---|---|
| | | Gadolinium Content in Three Successive Lymph Node Stations [μmol] [% of dose/g of tissue] | | |
| Example | Time of Lymph Node Removal | Popliteal | Inguinal | Iliac |
| 7 | 30 minutes | 452 μmol/l 13.1% | 181 μmol/l 5.2% | 228 μmol/l 6.6% |
| 6b | 30 minutes | 442 mol/l 12.6% | 339 μmol/l 9.6% | 322 μmol/l 9.1% |
| 5e | 30 minutes | 581 μmol/l 16.9% | 166 μmol/l 4.8% | 111 μmol/l 3.2% |
| 3c | 90 minutes | 346 μmol/l 10.1% | 184 μmol/l 5.4% | 171 μmol/l 5.0% |

EXAMPLE 23

Lymph Node Visualization (MRT) after Interstitial Administration of Contrast Medium MR images of popliteal, inguinal and iliac lymph nodes both before (Precontrast) and 15 or 30 minutes after subcutaneous administration (guinea pigs, hind paw, interdigital space) of the substance of Example 5e or of Example 3c (in each case 10 μmol of Gd/kg of body weight) were taken. The $T_1$-weighted, gradient echo images (TR 10 ms, flash outphase, TE 5 ms, α 40°) illustrate the strong signal increase in the various lymph nodes of the injected body side in comparison to the non-injected body side or to the precontrast image.

EXAMPLE 24

Retention of the Opacifying Metal at the Injection Site

After s.c. administration of 10 μmol of total gadolinium/kg of body weight in the guinea pig paw, the retention of metal at the injection site was studied at different times.

| Substance | Gadolinium Content at the Injection Site (Paw) [% of dose] | | |
|---|---|---|---|
| Example | 30 min. p.i. | 90 min. p.i. | 7 days p.i. |
| 7 | 54.2% | 36.8% | 1.3% |
| 6b | 66.4% | 26.1% | 0.6% |
| 5e | 8.5% | 9.4% | — |
| 3c | 6.5% | 4.9% | 1.7% |

EXAMPLE 25

Organ Distribution of the Contrast Medium After s.c. Administration

After subcutaneous administration of 10 μmol of total gadolinium/kg of body weight in the hind paw of stimulated guinea pigs (complete Freund adjuvant; 0.1 ml i.m in the right and left lower leg in each case; 2 weeks before the test are administered), the retention of the metal in the ell as in the kidneys and spleen was examined 7 days administration.

| Substance | Gadolinium Content in Various organs [% of dose] | | |
|---|---|---|---|
| Example | Liver | Kidneys | Spleen |
| 7 | 6.2% | 0.2% | 0.0% |
| 6b | 1.5% | 0.1% | 0.0% |
| 3c | 1.3% | 0.1% | 0.0% |

EXAMPLE 26

Relaxivity of Compounds According to the Invention

| Substance | R1 [L/mmol · sec] at 0.47 T and 37° C. | |
|---|---|---|
| Example | Water | Plasma |
| 7 | 18.1 | 21.0 |
| 6b | 11.6 | 13.3 |
| 5e | 12.4 | 30.3 |
| 3c | 14.0 | 21.0 |
| 1c | 13.8 | 25.7 |
| 2c | 11.8 | 19.6 |
| 4c | 14.4 | 21.9 |
| 10c | 21.6 | 27.8 |

EXAMPLE 27

Compatibility of Compounds According to the Invention

| Substance Example | LD 50 [mmol of Gd/kg of body weight] |
|---|---|
| 2c | 3 |
| 3c | 8 |
| 4c | 0.3 |
| 5e | 15 |

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A metal complex of the formula I

(I)

in which

K is a complexing agent or a metal complex of the formula II

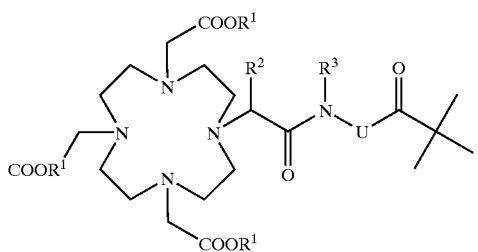

(II)

where

R$^1$ is a hydrogen atom or a metal ion equivalent of atomic numbers 21–29, 31, 32, 37–39, 42–44, 49 or 57–83, R$^2$ and R$^3$ are independently a hydrogen atom, a C$_1$–C$_7$ alkyl group, a benzyl group, a phenyl group, —CH$_2$OH or —CH$_2$—OCH$_3$, U has the same meaning as L, where L and U, independently of one another, can be the same or different, A is a —L—R$^F$ group, a hydrogen atom, or a straight-chain or branched C$_1$–C$_{30}$ alkyl group, which optionally is interrupted by 1–15 oxygen atoms and/or optionally is substituted with 1–10 hydroxy groups, 1–2 COOH groups, a phenyl group, a benzyl group and/or 1–5 —OR$^4$ groups, where R$^4$ is a hydrogen atom or a C$_1$–C$_7$ alkyl radical, L is a straight-chain or branched C$_1$–C$_{30}$ alkylene group, which optionally is interrupted by: 1–10 oxygen atoms; 1–5 —NH—CO—groups; 1–5—CO—NH— groups; a phenylene group that is optionally substituted by a COOH group; 1–3 sulfur atoms; 1–2—N(B$^1$)—SO$_2$— groups; and/or 1–2—SO$_2$—N(B$^1$)— groups; where B$^1$ independently is as defined for A; and/or the alkylene group optionally is substituted with a R$^F$ group; and R$^F$ is a straight-chain or branched perfluorinated alkyl radical of the formula C$_n$F$_{2n}$X, where $4 \leq n \leq 20$ and X is a terminal fluorine atom, chlorine atom, iodine atom or hydrogen atom, and any —COOH acid groups in the complex optionally are in the form of a salt of an organic and/or inorganic base or amino acid or amino acid amide.

2. A metal complex according to claim 1, wherein at least one $^1$ is a metal ion equivalent of an element of atomic number 21–29, 39, 42, 44 or 57–83.

3. A metal complex according to claim 1, wherein at least one R$^1$ is a metal ion equivalent of an element of atomic number 27, 29, 31, 32, 37–39, 43, 49, 62, 64, 70, 75 or 77.

4. A metal complex according to claim 1, wherein R$^2$, R$^3$ and R$^4$, independently of one another, are hydrogen or a C$_1$–C$_4$ alkyl group.

5. A metal complex according to claim 1, wherein A is hydrogen, C$_1$–C$_{15}$ alkyl, C$_2$H$_4$—O—CH$_3$, C$_3$H$_6$—O—CH$_3$, C$_2$H$_4$—O—(C$_2$H$_4$—O)$_t$—C$_2$H$_4$—OH, C$_2$H$_4$—O—(C$_2$H$_4$—O)$_t$—C$_2$H$_4$—OCH$_3$, C$_2$H$_4$OH, C$_3$H$_6$OH, C$_4$H$_8$OH, C$_5$H$_{10}$OH, C$_6$H$_{12}$OH, C$_7$H$_{14}$OH, CH(OH)CH$_2$OH, CH(OH)CH(OH)CH$_2$OH, CH$_2$[CH(OH)]$_u$CH$_2$OH, CH[CH$_2$(OH)]CH(OH)CH$_2$OH, C$_2$H$_4$CH(OH)CH$_2$OH, (CH$_2$)$_s$COOH, C$_2$H$_4$—O—(C$_2$H$_4$—O)$_t$—CH$_2$COOH, C$_2$H$_4$—O—(C$_2$H$_4$—O)$_t$—C$_2$H$_4$—C$_n$F$_{2n}$X, where s is an integer of 1 to 15, t is an integer of 0 to 13, u is an integer of 1 to 10, n is an integer of 4 to 20, and X is a fluorine, chlorine, bromine or iodine atom, or a branched isomer of one of these groups.

6. A metal complex according to claim 1, wherein A is hydrogen, C$_1$–C$_{10}$ alkyl, C$_2$H$_4$—O—CH$_3$, C$_3$H$_6$—O—CH$_3$, C$_2$H$_4$—O—(C$_2$H$_4$—O)$_x$—C$_2$H$_4$—OH, C$_2$H$_4$—O—(C$_2$H$_4$—O)$_x$O$_2$H$_4$—OCH$_3$, C$_2$H$_4$OH, C$_3$H$_6$OH, CH$_2$[CH(OH)]$_y$CH$_2$OH, CH[CH$_2$(OH)]CH(OH)CH$_2$OH, (CH$_2$)$_w$COOH, C$_2$H$_4$—O—(C$_2$H$_4$—O)$_x$CH$_2$COOH, C$_2$H$_4$—O—(C$_2$H$_4$—O)$_x$—C$_2$H$_4$—C$_p$F$_{2p}$X)

where x is an integer of 0 to 5, y is an integer of 1 to 6, w is an integer of 1 to 10, p is an integer of 4 to 15, and X stands for a fluorine atom, or a branched isomer of one of these groups.

7. A metal complex according to claim 1, wherein L is

α-(CH$_2$)$_k$-β

α-CH$_2$—CH$_2$—(O—CH$_2$—CH$_2$—)$_r$-β

α-CH$_2$—(O—CH$_2$—CH$_2$—)$_r$-62 )

α-CH$_2$—NH—CO-β

α-CH$_2$—CH$_2$—NH—SO$_2$-β

α-CH$_2$—NH—CO—CH$_2$—N(CH$_2$COOH)—SO$_2$-β

α-CH$_2$—NH—CO—CH$_2$—N(C$_2$H$_5$)—SO$_2$-β

α-CH$_2$—NH—CO—CH$_2$—N(C$_{10}$H$_{21}$)—SO$_2$-62

α-CH$_2$—NH—CO—CH$_2$—N(C$_6$H$_{13}$)—SO$_2$-β

α-CH$_2$—NH—CO—(CH$_2$)$_{10}$—N(C$_2$H$_5$)—SO$_2$-β

α-CH$_2$—NH—CO—CH$_2$—N(—CH$_2$—C$_6$H$_5$)—SO$_2$-β

α-CH$_2$—NH—CO—CH$_2$—N(—CH$_2$—CH$_2$—OH)SO$_2$-β

α-CH$_2$—NHCO—(CH$_2$)$_{10}$—S—CH$_2$CH$_2$-β

α-CH$_2$NHCOCH$_2$—O—CH$_2$CH$_2$-β

α-CH$_2$—CH$_2$NHCOCH$_2$—O—CH$_2$CH$_2$-β

α-CH$_2$—(CH$_2$—CH$_2$—O)$_r$—(CH$_2$)$_3$NHCO—CH$_2$—O—CH$_2$CH$_2$-β

α-CH$_2$NHCO(CH$_2$)$_{10}$—O—CH$_2$CH$_2$-β

α-CH$_2$CH$_2$NHCO(CH$_2$)$_{10}$—O—CH$_2$CH$_2$-β

α-CH$_2$—C$_6$H$_4$—O—CH$_2$CH$_2$-β wherein the phenylene group is 1,4- or 1,3-linked α-CH$_2$—O—CH$_2$—C(CH$_2$—OCH$_2$CH$_2$C$_6$F$_{13}$)$_2$—CH$_2$—OCH$_2$—CH$_2$-β

α-CH$_2$—NHCOCH$_2$CH$_2$CON—CH$_2$CH$_2$NHCOCH$_2$N(C$_2$H$_5$)SO$_2$C$_8$F$_{17}$β

α-CH$_2$—CH$_2$NHCOCH$_2$N(C$_2$H$_5$)—SO$_2$-β

α-CH$_2$—O—CH$_2$—CH(OC$_{10}$H$_{21}$)—CH$_2$—O—CH$_2$CH$_2$-β

α-(CH₂NHCO)₄—CH₂O—CH₂CH₂-β
α-(CH₂NHCO)₃—CH₂O—CH₂CH₂-β
α-CH₂—OCH₂C(CH₂OH)₂—CH₂—O—CH₂CH₂-β

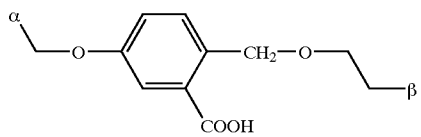

α-CH₂NHCOCH₂N(C₆H₅)—SO₂-β
α-NHCO—CH₂—CH₂-β
α-NHCO—CH₂—O—CH₂CH₂-β
α-NH——O-β
α-NH—CO—CH₂—N(CH₂COOH)—SO₂-β
α-NH—CO—CH₂—N(C₂H₅)—SO₂-β
α-NH—CO—CH₂—N(C₁₀H₂₁)—SO₂-β
α-NH—CO—CH₂—N(C₆H₁₃)—SO₂-β
α-NH—CO—(CH₂)₁₀—N(C₂H₅)—SO₂-β
α-NH—CO—CH₂—N(—CH₂—C₆H₅)—SO₂-β
α-NH—CO—CH₂—N(—CH₂—CH₂—OH)SO₂-β
α-NH—CO—CH₂-β
α-CH₂—O—C₆H₄—O—CH₂—CH₂-β
α-CH₂—C₆H₄—O—CH₂—CH₂-β
α-N(C₂H₅)—SO₂-β
α-N(C₆H₅)—SO₂-β
α-N(C₁₀H₂₁)—SO₂-β
α-N(C₆H₁₃)—SO₂-β
α-N(C₂H₄OH)—SO₂-β
α-N(CH₂COOH)—SO₂-β
α-N(CH₂C₆H₅)—SO₂-β
α-N—[CH(CH₂OH)₂]—SO₂-β, or
α-N—[CH(CH₂OH)CH(OH)(CH₂OH)]—SO₂-β
wherein
k is an integer of 1 to 15, and
r is an integer of 1 to 6.

8. A metal complex according to claim 1, wherein L is
α-CH₂—O—CH₂CH₂-β,
α-CH₂—CH₂—(O—CH₂—CH₂—)$_y$-β,
α-CH₂—(O—CH₂—CH₂—)$_y$-β,
α-CH₂—CH₂—NH—SO₂-β,
α-CH₂NHCOCH₂—O—CH₂CH₂-β,
α-CH₂—CH₂NHCOCH₂—O—CH₂CH₂-β,
α-CH₂—(CH₂—CH₂—O)$_y$—(CH₂)₃NHCO—CH₂—O—CH₂CH₂-β,
α-CH₂NHCO(CH₂)₁₀—O—CH₂CH₂-β,
α-CH₂CH₂NHCO(CH₂)₁₀—O—CH₂CH₂-62,
α-CH₂—O—CH₂—CH(OC₁₀H₂₁)—CH₂—O—CH₂CH₂-β,
α-CH₂—O—C₆H₄—O—CH₂CH₂-β or
α-CH₂—C₆H₄—O—CH₂—CH₂-β
wherein y is an integer of 1 to 6.

9. A metal complex according to claim 1, wherein $R^F$ is a straight-chain or branched perfluorinated alkyl of the formula $C_pF_{2p}X$, where 4 is equal to or less than p, which is equal to or less than 15, and X stands for a terminal fluorine atom.

10. A method for producing a contrast medium for use in NMR or x-ray diagnosis which comprises incorporating a metal complex according to claim 2 in the medium.

11. A method for producing a contrast medium for use in radiodiagnosis or radiotherapy which comprises incorporating a metal complex according to claim 3 in the medium.

12. A method for producing a contrast medium for use in indirect lymphography which comprises incorporating a metal complex according to claim 1 in the medium.

13. A method for producing a lymph-specific contrast medium for use in diagnosis of changes of the lymphatic system which comprises incorporating a metal complex according to claim 1 in the medium.

14. A method for producing a contrast medium for use in intravenous lymphography which comprises incorporating a metal complex according to claim 1 in the medium.

15. A pharmaceutical composition which comprises at least one physiologically compatible metal complex according to claim 1.

16. A method for NMR or x-ray diagnosis which comprises administering to a patient a contrast medium comprising a metal complex according to claim 2 and conducting an NMR or x-ray diagnosis on the patient.

17. A method for radiodiagnosis or radiotherapy which comprises administering to a patient a contrast medium comprising a metal complex according to claim 3 and conducting radiodiagnosis or radiotherapy on the patient.

18. A method for lymphography which comprises administering to a patient a contrast medium comprising a metal complex according to claim 1 and conducting a lymphography method on the patient.

19. A process for preparing a metal complex of the formula I of claim 1, which comprises:

reacting a compound of the formula IIIb

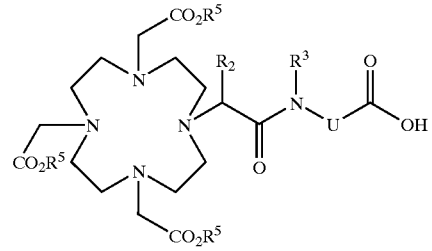

(IIIb)

in which $R^5$ is a metal ion equivalent of atomic numbers 21–29, 31, 32, 37–39, 42–44, 49 or 57–83 or a carboxyl protective group, in optionally activated form, with an amine of the formula IV

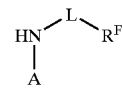

(IV)

in which A, L and $R^F$ have the above-indicated meanings, by a coupling reaction, and optionally subsequently cleaving optionally present protective groups to provide a compound of the formula Ia

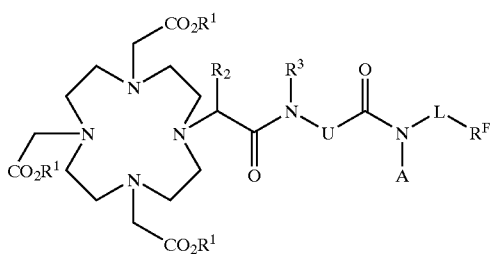

(Ia)

in which radicals $R^2$, $R^3$, U, L, $R^F$ and A have the above-indicated meanings, and $R^1$ stands for a metal ion equivalent of atomic numbers 21–29, 31, 32, 37–39, 42–44, 49 or 57–83, if $R^5$ has the meaning of a protective group, reacting the compound of formula Ia after cleaving of the protective groups with at least one metal oxide or metal salt of an element of atomic numbers 21–29, 31, 32, 37–39, 42–44, 49 or 57–83, and substituting optionally present acid hydrogen atoms by cations of an inorganic and/or organic base, amino acid or amino acid amide.

* * * * *